US010530976B2

(12) United States Patent
Takeuchi et al.

(10) Patent No.: US 10,530,976 B2
(45) Date of Patent: Jan. 7, 2020

(54) ENDOSCOPE PROBES AND SYSTEMS, AND METHODS FOR USE THEREWITH

(71) Applicant: CANON U.S.A., INC., Melville, NY (US)

(72) Inventors: Seiji Takeuchi, Newton, MA (US); Jacob Schieffelin Brauer, Cambridge, MA (US); Anderson Mach, Cambridge, MA (US); Badr Elmaanaoui, Belmont, MA (US); Sarika Verma, Reading, MA (US); Kenji Yamazoe, Tochigi (JP); Toshiyuki Sudo, Tokyo (JP); Michio Ishikawa, Tokyo (JP)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 16/216,847

(22) Filed: Dec. 11, 2018

(65) Prior Publication Data

US 2019/0174038 A1 Jun. 6, 2019

Related U.S. Application Data

(63) Continuation of application No. 15/229,768, filed on Aug. 5, 2016, now Pat. No. 10,194,065.

(Continued)

(51) Int. Cl.
*G02B 23/26* (2006.01)
*H04N 5/225* (2006.01)
(Continued)

(52) U.S. Cl.
CPC ....... *H04N 5/2256* (2013.01); *G02B 23/2461* (2013.01); *G02B 23/26* (2013.01);
(Continued)

(58) Field of Classification Search
CPC ............ G02B 23/2461; G02B 23/26; G02B 27/4227; G02B 5/008; G02B 5/124;
(Continued)

(56) References Cited

U.S. PATENT DOCUMENTS 5,565,983 A * 10/1996 Barnard .................. G01J 3/02
356/328
6,488,414 B1 12/2002 Dawes et al.
(Continued)

FOREIGN PATENT DOCUMENTS

WO 2013/108209 A1 7/2013

OTHER PUBLICATIONS

Masud Mansuripur, "Classical Optics and its Applications", Cambridge University Press, 2002, pp. 224-229 (plus title and copyright pages).

(Continued)

*Primary Examiner* — Michael P Stafira
(74) *Attorney, Agent, or Firm* — Canon U.S.A., Inc. IP Division

(57) ABSTRACT

The present disclosure provides apparatuses and methods for color imaging and an increased field of view using spectrally encoded endoscopy techniques. At least one of the apparatuses includes an illumination unit having two or more spectrally dispersive gratings positioned, for example, on different planes or on the same plane but having grating vectors at an angle to each other such that bands of spectrally dispersed light propagating from the gratings propagate on different planes.

15 Claims, 21 Drawing Sheets

Related U.S. Application Data

(60) Provisional application No. 62/314,840, filed on Mar. 29, 2016, provisional application No. 62/201,410, filed on Aug. 5, 2015.

(51) Int. Cl.
  *G02B 27/42* (2006.01)
  *G02B 23/24* (2006.01)
  *A61B 1/00* (2006.01)
  *A61B 5/00* (2006.01)

(52) U.S. Cl.
  CPC ...... *G02B 27/4227* (2013.01); *A61B 1/00096* (2013.01); *A61B 5/0075* (2013.01); *A61B 5/0084* (2013.01); *H04N 2005/2255* (2013.01)

(58) Field of Classification Search
  CPC .... G02B 6/0001; G02B 6/0021; G02B 6/003; G02B 6/0036; G02B 6/0041; G02B 6/0061; G02B 6/0073; G02B 6/136; G02B 13/06; G02B 13/16; G02B 19/0014; G02B 19/0076; G02B 1/105; G02B 1/14; G02B 27/0927; G02B 27/0994; G02B 27/22; G02B 27/2257; G02B 27/2292; G02B 3/0056; G02B 5/003; G02B 5/02; G02B 5/0816; G02B 5/0891; G02B 5/09; G02B 5/10; G02B 6/0008; G02B 6/0053; G02B 6/3809; G02B 6/3849; G02B 6/4298; H04N 2005/2255; H04N 5/2254; H04N 5/23238; H04N 5/2171; H04N 5/225; H04N 5/2253; H04N 5/2256; H04N 5/2258; H04N 5/232; H04N 5/23232; H04N 9/31; H04N 9/3144; H04N 9/3147; H04N 5/228; H04N 5/2351; H04N 5/30; H04N 5/3415; A61B 1/00096; A61B 2560/045; A61B 5/0004; A61B 5/0015; A61B 5/0075; A61B 5/0084; A61B 5/14503; A61B 5/14532; A61B 5/1473; A61B 5/14865; A61B 5/683; A61B 5/6849; A61B 17/7068; A61B 1/041; A61B 5/0031; A61B 8/00; A61B 8/145; A61B 8/4281; A61B 8/4411; A61B 8/4427; A61B 8/4461; A61B 8/4494; A61B 8/54; A61B 8/56; G01N 21/658; G01N 15/06; G01N 2015/0687; G01N 2015/0693; G01N 21/17; G01N 21/53; G01N 21/64; G01N 21/85; G01N 2201/0642; G01N 27/12; G01N 29/221; G01N 29/262; G01J 1/0214; G01J 1/0407; G01J 3/44

See application file for complete search history.

(56) References Cited

U.S. PATENT DOCUMENTS

| | | |
|---|---|---|
| 6,522,403 B2 | 2/2003 | Wilson et al. |
| 7,181,106 B2 | 2/2007 | Ushiro et al. |
| 7,551,293 B2 | 6/2009 | Yelin et al. |
| 7,894,058 B2 | 2/2011 | Wilson et al. |
| 9,046,419 B2 | 6/2015 | Yelin et al. |
| 9,295,391 B1 | 3/2016 | Tearney et al. |
| 2007/0276187 A1 | 11/2007 | Wiklof et al. |
| 2009/0153932 A1 | 6/2009 | Davis et al. |
| 2011/0275899 A1* | 11/2011 | Tearney .................. A61B 1/07 600/160 |
| 2014/0071238 A1 | 3/2014 | Mertens et al. |
| 2014/0378846 A1 | 12/2014 | Hosoda et al. |
| 2015/0105622 A1 | 4/2015 | Yelin et al. |
| 2015/0131098 A1 | 5/2015 | Yang et al. |
| 2015/0231841 A1 | 8/2015 | Tearney et al. |
| 2016/0341951 A1 | 11/2016 | Tearney et al. |
| 2016/0349417 A1 | 12/2016 | Tearney et al. |

OTHER PUBLICATIONS

Noboru Ohta, "Color Engineering (Second Publication)", published by Tokyo Denki University Press.

* cited by examiner

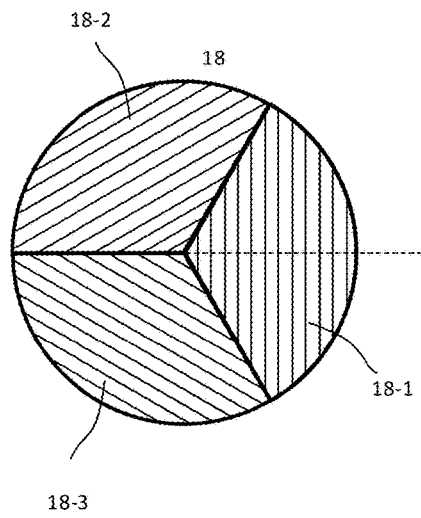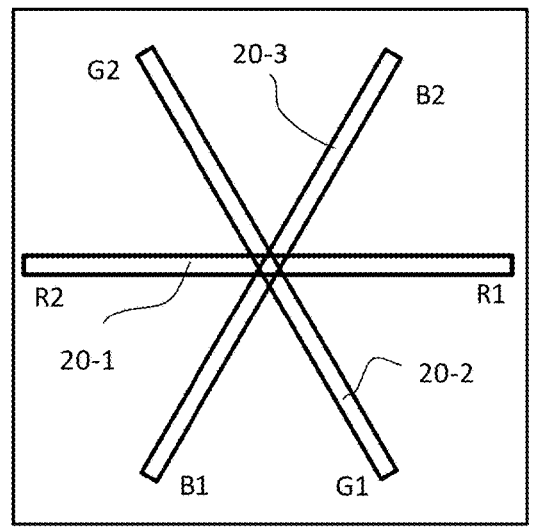
FIG. 17    FIG. 18
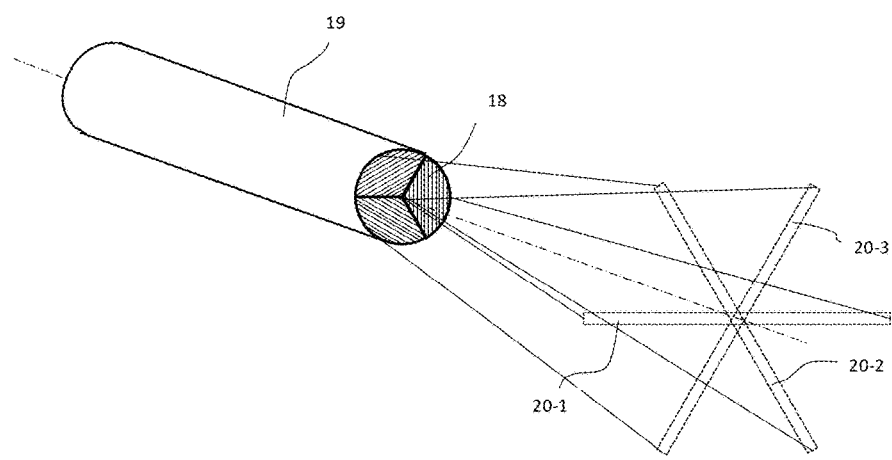
FIG. 19

| | 19 | 23 |
|---|---|---|
| Glass Material | SNPH2_OHARA | SFSL5_OHARA |
| Refractive Index | 1.936 | 1.49 |

Calculation process for three bands, X, Y, Z (Billmeyer, Jr & Saltzman, 1981)

ENDOSCOPE PROBES AND SYSTEMS, AND METHODS FOR USE THEREWITH

CROSS-REFERENCE TO RELATED APPLICATIONS

This application is a continuation, and claims the benefit, of U.S. patent application Ser. No. 15/229,768, presently pending and filed on Aug. 5, 2016, and claims priority to U.S. Patent Application Ser. No. 62/201,410, filed Aug. 5, 2015, the entire disclosures of which applications are incorporated herein by reference, and this application relates, and claims priority to, U.S. Patent Application Ser. No. 62/314,840, filed Mar. 29, 2016, the disclosure of which is incorporated by reference herein in its entirety.

FIELD OF THE INVENTION

The present disclosure relates generally to the field of endoscopy and, more particularly to, e.g., apparatus and methods for color imaging and increased field of view using spectrally encoded endoscopy techniques.

BACKGROUND

Spectrally encoded endoscope ("SEE") is an endoscope technology which uses a broadband light source, a rotating grating and a spectroscopic detector to encode spatial information on a sample. When illuminating light to the sample, the light is spectrally dispersed along one illumination line, such that the dispersed light illuminates a specific position of the illumination line with a specific wavelength. When the reflected light from the sample is detected with the spectrometer, the intensity distribution is analyzed as the reflectance along the line. By rotating or swinging the grating back and forth to scan the illumination line, a two-dimensional image of the sample is obtained. SEE techniques have been described in, e.g., U.S. Patent Publication Nos. 2007/0233396 and 2008/0013960, which are herein incorporated by reference in their entireties.

Doctors will often use color information as cues to diagnosis. However, by using wavelength information to encode spatial location, SEE images cannot provide color images as simply, and important color information may be lost. Color SEE can be realized by illuminating the grating with several different incidence angles, each with light of a respective wavelength band of color, so that light with color of red, green and blue each spectrally disperses on to the sample on one line and overlapping each other. Spectrally encoded endoscope had one grating at the tip to disperse light in one dimension and in one plane. It required three fibers with a different wavelength band. This is described in U.S. Patent Publication No. 2011/0237892, which is herein incorporated by reference in its entirety, and by D. Kang et al., Opt. Exp. Vol. 17, No. 17, 15239 (2009).

However, the use of multiple fibers potentially enlarges the diameter of the probe and it complicates the system at the proximal end when a rotary junction is used since, for example, the probe needs to be disconnected for an exchange of the probe and each fiber requires a separate connector at the proximal end.

Further, existing spectrally encoded endoscopes irradiate the sample with one spectral bandwidth of light with approximately the same incident angle. This limited the dispersion of the light and limited the field of view of the spectrally encoded endoscope. However, an increased field of view is important for some endoscopic applications, and when increasing the field of view where the diffraction overlaps in one plane (or one line on the sample) there is an increase in crosstalk when collecting light and recreating the image from spectrally encoded light.

Accordingly, there may be a need to address and/or overcome at least some of the issues described herein above.

SUMMARY

One or more embodiments of the present disclosure relate to an apparatus that comprises an illumination unit having at least a first spectrally dispersive grating and a second spectrally dispersive grating structured and positioned, for example, on different planes or on the same plane but having grating vectors at an angle to each other such that a first band of spectrally dispersed light propagating from the first spectrally dispersive grating propagates on a different plane than a second band of spectrally dispersed light propagating from the second spectrally dispersive grating. The apparatus also comprises one or more detection waveguides configured to receive a first reflected light and a second reflected light reflected by a sample; and one or more detection units configured to: detect and correlate the first and second reflected lights and form one or more images with information of at least two colors of light, detect and connect a field of view of light and form one or more images with connected field of view, or detect and correlate the first and second reflected lights and form one or more images with information obtained by the one or more detection units at different times. The apparatus as described herein is configured such that the first and second bands of spectrally dispersed light are spatially separated when incident on the sample.

In certain embodiments, the first and second bands of spectrally dispersed light: illuminate a same position on the sample at different times when the at least a first and a second spectrally dispersive gratings are rotated, cover different diffraction angles, or illuminate the same azimuthal angle at different times when the at least a first and a second spectrally dispersive gratings are rotated.

In some embodiments, the first reflected light is a light reflected from an anatomical structure after the first band of spectrally dispersed light illuminates the structure, and the second reflected light is a light reflected from an anatomical structure after the second band of spectrally dispersed light illuminates the structure. A color image may be formed from the first and the second reflected lights (and in some embodiments, a third and optionally a fourth or more reflected lights) by correlating the different reflected lights based on their location and time.

In some embodiments, the apparatus has one single mode fiber connected to the rotating distal tip. The two or more different gratings are oriented so that the diffractions are dispersed to different planes of diffraction.

The apparatus may have two or more gratings with each diffraction pattern dispersing in different planes. Having two or more gratings provides flexibility to the design of the apparatus, allowing a wider field of view by each grating covering a different angle of view. Another advantage is that the gratings are illuminated at the same time, but since the gratings disperse to different angles, and thus since the light originating from each different grating can be collected at a different timing or at different timings, crosstalk of the different light illuminating with a same wavelength can be minimized.

The different gratings can be used to illuminate the same position at a different time with a different wavelength band of the light which allows color configuration of the apparatus.

Some embodiments as disclosed herein comprise a probe comprising: a light guiding component, a light focusing component, a rotational element, and a grating configuration that comprises at least three spectrally dispersive grating patterns such that bands of spectrally dispersed light propagating from the at last three spectrally dispersive grating patterns propagate on different planes and are incident on a sample at different spatial positions. The three spectrally dispersive grating patterns may each be on different planes. Alternatively, the three spectrally dispersive grating patterns may have grating vectors at an angle to each other.

Some embodiments as disclosed herein provide an apparatus comprising: an illumination unit comprising at least a first spectrally dispersive grating, wherein the illumination unit is structured and positioned such that a first band of spectrally dispersed light propagating from the illumination unit propagates on a different plane than a second band of spectrally dispersed light propagating from the illumination unit, one or more detection waveguides configured to receive a first reflected light and a second reflected light reflected by a sample; and one or more detection units configured to: detect and correlate the first and second reflected lights and form one or more images with information of at least two colors of light, detect and connect a field of view of light and form one or more images with the connected field of view, or detect and correlate the first and second reflected lights and form one or more images with information obtained by the one or more detection units at different times, wherein the probe is configured such that the first and second bands of spectrally dispersed light are spatially separated when incident on the sample.

Some embodiments as disclosed herein provide an endoscope system comprising: a probe; an irradiation unit configured to irradiate an observation region by a focal point spectrum extending one-dimensionally from the probe; and an acquisition unit configured to acquire a reflectivity distribution of the observation region by the focal point spectrum being moved along a different dimension, and measuring time-sequence spectrums of reflected light, wherein the focal point spectrum is generated by a diffractive grating having diffraction angles in multiple directions two-dimensionally, wherein the diffracted light from the diffractive grating is diffracted in different directions for each of three wavelengths regions corresponding to each of the three primary colors of light, Red, Green, and Blue, and three focal point spectrums separated in three directions on the observation region, by wavelength diffraction according to a diffraction angle, wherein the movement of the focal point spectrum is due to rotational action of the probe, and wherein the three focal point spectrums are superimposed in time-sequence due to the rotation of the probe, and color information of reflected light in the observation region is acquired from the amount of rotation of the probe and the measurement results of the focal point spectrum.

These and other features of the embodiments as will be apparent are set forth and described herein.

BRIEF DESCRIPTION OF THE DRAWINGS

A detailed description of various embodiments is provided herein below with reference, by way of example, to the following drawings. The skilled person in the art will understand that the drawings, described below, are for illustration purposes only. The drawings are not intended to limit the scope of the teachings of the present disclosure in any way.

FIG. 2(a) is a schematic diagram of an exemplary embodiment of a probe tip. FIG. 2(b) is the front view of the probe tip of FIG. 2(a). FIG. 2(c) is a schematic diagram of an exemplary embodiment of a probe tip. FIG. 2(d) is the front view of the probe tip of FIG. 2(c).

FIG. 7(a) is a schematic diagram of an exemplary embodiment of a probe tip. FIG. 7(b) is the front view of the probe tip of FIG. 7(a).

FIG. 11(a) is a schematic diagram of an exemplary embodiment of a probe tip. FIG. 11(b) is the front view of the probe tip of FIG. 11(a).

FIG. 13(a) is a schematic diagram of an exemplary embodiment of a probe tip. FIG. 13(b) is the front view of the probe tip of FIG. 13(a). FIG. 13(c) is the front view of the probe tip of FIG. 13(a) where the grating vectors are shown.

FIG. 17 is an enlarged frontal diagram of a diffraction grating.

FIG. 18 illustrates an illumination light distribution on a plane of a subject.

FIG. 19 illustrates an illumination light distribution on a plane of a subject.

Figure 1:
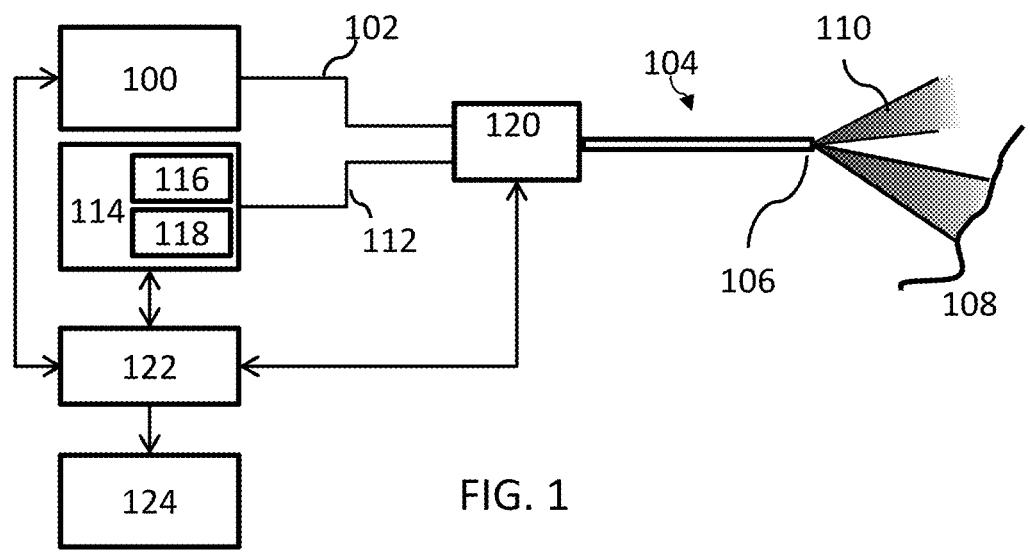
FIG. 1 is a schematic diagram of an exemplary embodiment of a system containing a SEE apparatus according to an exemplary embodiment of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure as defined by the appended paragraphs.

It will be understood that the drawings are exemplary only and that all reference to the drawings is made for the purpose of illustration only, and is not intended to limit the scope of the embodiments described herein below in any way.

DETAILED DESCRIPTION

There is provided herewith an endoscope, method of use, and optical apparatus that is used to form multiple color images.

First Embodiment

FIG. 1 is a schematic of an exemplary system diagram. The system has a broadband light source 100 connected to a single mode fiber 102 and the fiber 102 is connected to a probe 104. The probe has an illumination unit or an illumination part 106, which illuminates the sample 108 with spectrally dispersed light 110. The probe 104 further has a detection waveguide, such as a detection fiber 112. The detection fiber 112 collects light from the sample 108 and transmits light to the detection unit 114. The detection unit 114 has a spectrometer 116 with a linescan camera 118 (see e.g., FIG. 1 diagrammatically illustrating the detection unit 114 including the spectrometer 116 and the linescan camera 118). As the illumination part 106 of the probe is rotated by a motor in an actuation unit 120 (e.g., positioned between the fiber 120 and the probe 104), a portion of the sample 108 is illuminated. The light with the information of the sample is collected with the detection fiber 112, and the detection unit 114 will send a corresponding signal to the processor 122 to reconstruct the image of the sample. The processor 122 controls the light source 100, detection unit 114 and actuator unit 120, so that the timings of the units are synchronized. The processed image is shown on the display monitor 124.

Figures 2A, 2B:
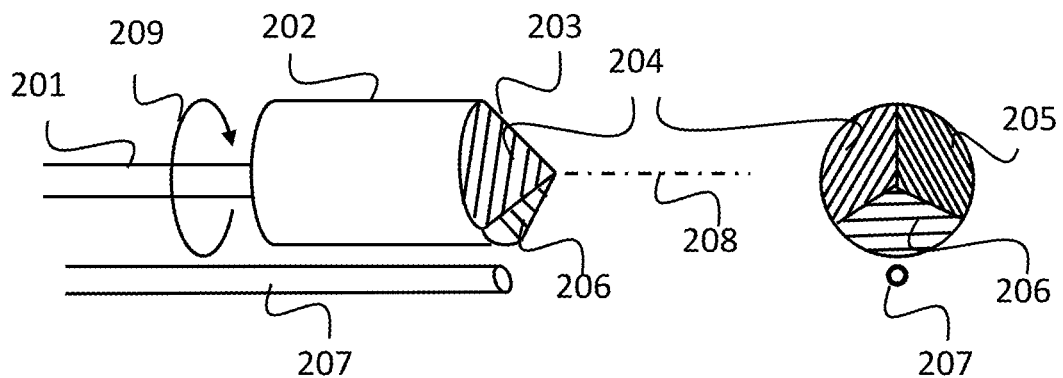
FIGS. 2(a), 2(b), 2(c) and 2(d).

An exemplary probe tip is shown in FIG. 2(a). The tip of the probe has an illumination part which consists or comprises of a single mode fiber 201 connected to a GRIN lens 202. There is a separate detection fiber 207. A tip of the illumination part 203 is shaped like a pyramid, each face having a grating. The pyramid tip 203 can be of a glass spacer oriented like a pyramid or the GRIN lens oriented like a pyramid (e.g., a GRIN lens being polished to a pyramid shape).

This exemplary probe tip having a single fiber can be particularly advantageous in a system since only a single fiber will connect, for example, to a rotating distal tip. This simplifies the connection of the probe typically requiring a one channel rotary junction.

As shown in the front view of FIG. 2(b), the gratings 204, 205, 206 are oriented such that the diffracted light from each grating will disperse light in a separate plane. The illumination part 201, 202 and the pyramid tip 203 are rotated with axis of rotation 208 as illustrated by the arrow 209 shown in FIG. 2(a).

Figures 2C, 2D:
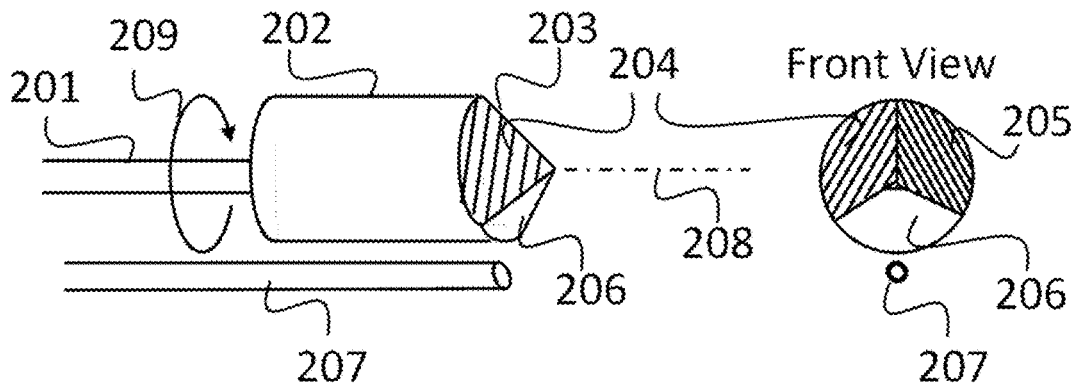

In this embodiment, the gratings 204, 205, 206 are designed in angle and pitch such that each of the gratings 204, 205, 206 will disperse light in such a way that one band of visible light will illuminate a certain angle range from the axis of rotation 208. In this embodiment, the gratings on the pyramid faces 204, 205 and 206 have lines aligned tangentially with respect to the axis of rotation. Thus, the diffraction of light directs the spectrally dispersed light in a line oriented radially with respect to the axis of rotation 208. The spectrally dispersed light propagates in three different planes, each of which includes the axis of rotation 208. In one or more embodiments, a grating may not be used. For example, a facet, such as the facet grating 206, may be coated with a light absorbing material (e.g., FIGS. 2(c) and 2(d)). In this embodiment, the gratings on the pyramid faces 204 and 205 have lines aligned tangentially with respect to the outer circle of GRIN lens. The diffraction of light directs the spectrally dispersed light in a line oriented radially with respect to the axis of rotation. The spectrally dispersed light propagates in two different planes, which includes the axis of rotation 208.

The detection fiber 207 in this embodiment is attached to a sheath (not shown) and does not rotate with the illumination part 203. The detection fiber 207 may also or alternatively be encased in a smaller lumen of a double lumen sheath, with the illumination part 203 rotating in the larger lumen, such that the detection fiber 207 does not rotate with the illumination part 203.

Figure 3:
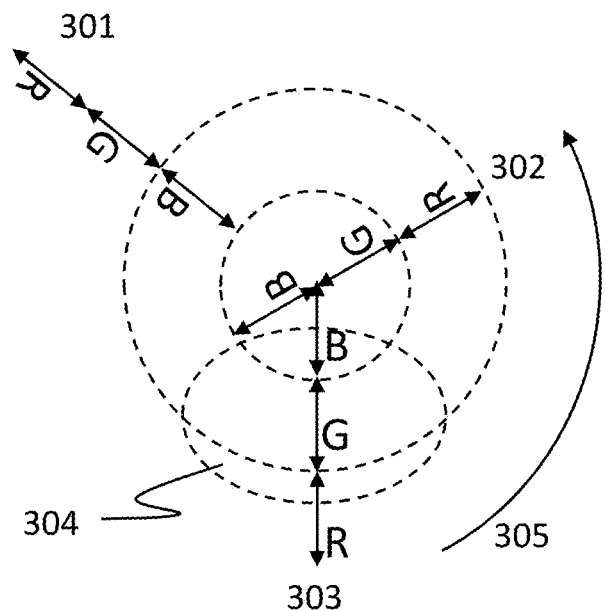
FIG. 3 is a schematic showing the illumination light pattern on a screen perpendicular to the rotation axis, observed from the direction of the probe for light from the probe shown in FIG. 2(a).

Motion of illumination light is explained using FIG. 3. FIG. 3 shows the illumination light pattern on a screen perpendicular to the rotation axis (e.g., the axis of rotation 208), observed from the direction of the probe for light from the probe shown in FIG. 2(a). The sets of 3 arrows, 301, 302 and 303 are the spectrally dispersed illumination light on the screen (not shown in FIG. 2(a)), each originating from gratings of respective facet on the pyramid. The arrows with letters R, G and B illustrate the line of dispersed light with blue, green and red wavelength bands, respectively. The detection fiber 207 has its tip polished in an angle such that the light from certain angle is collected. In this embodiment, the detection fiber 207 collects the light scattered or reflected from the field of view 304. As the illumination probe is rotated in the direction of the illumination light 305, illustrated by 301, 302 and 303, the field of view 304 of the detection fiber 207 will be illuminated by at least red light of 302 (R), green light of 303 (G) and blue light of 301 (B), sequentially. As the probe is rotated, this pattern will be repeated.

Figure 4:
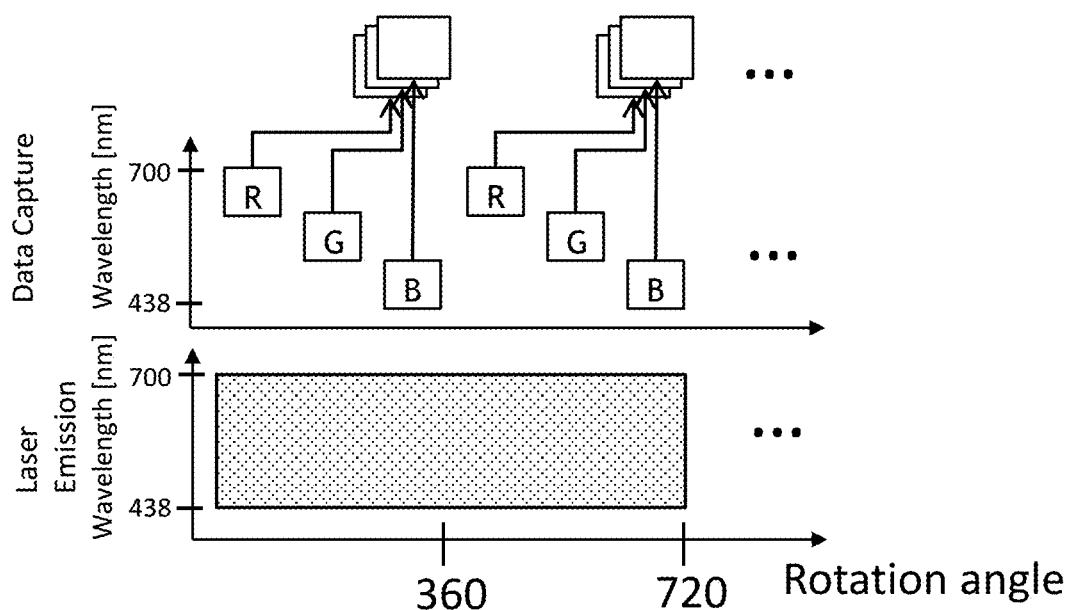
FIG. 4 is an exemplary data processing chart (top half) and timing chart (bottom half) for light from the probe of FIG. 2(a) that is sent to a line scan camera.

An exemplary data processing and timing chart is shown in FIG. 4. The horizontal axis of the graph is a rotation angle of the illumination fiber, which is also correlated with time. The vertical axis is the wavelength. (Notice the wavelength is longer at the bottom to match the field of view 304 in FIG. 3.) The bottom portion of the graph shows the laser emission of the light source. The hatched area on the bottom graph shows that the light of the broad band with wavelength range of 438 nm to 700 nm is continuously emitted and delivered to the probe. The top portion of the graph of FIG. 4 shows the data that can be used coming from the line scan camera. For this chart, the detection unit (e.g., the detection unit 114) is a spectrometer (e.g., the spectrometer 116) with a linescan camera (e.g., the linescan camera 118) such that the detected light is dispersed with respect to the wavelength of light on the linescan camera (e.g., the linescan camera 118). The line data of light intensity is lined up vertically and as the time proceeds, the next line date is lined up to the right of the preceding line data. The top graph has the vertical axis as wavelength as aforementioned but pixel coordinates on the line scan camera (e.g., the linescan camera 118) may be used once the wavelength of the spectrometer (e.g., the spectrometer 116) is calibrated.

When the light on the illumination line 302 of FIG. 3 is illuminating the field of view 304, a red portion of the data from the linescan camera (e.g., the linescan camera 118), marked 'R' in FIG. 4 is extracted. As the rotation proceeds and the illumination line of 303 is illuminating, the data corresponding to the green wavelength band, marked 'G' is extracted. Finally as the rotation proceeds and the illumination line of 301 is illuminating the field of view, the data corresponding to the blue wavelength band, marked 'B' is extracted. The extracted 3 frames are overlapped on one frame color image as data corresponding to red, green and blue components of the color image reconstruction. The same procedures are repeated for the consecutive frames as the probe is rotated continuously.

Since the light of the different bandwidths of the colors are collected at different timing, crosstalk of the different band can be minimized.

When the light on the illumination line 301 of FIG. 3 is illuminating the field of view 304, the full spectrum of the data from the linescan camera (e.g., the linescan camera 118) is extracted as the bottom part of one frame. As the rotation proceeds and the illumination line of 302 is illuminating, again, the full spectrum data is extracted but as the top part of the frame.

Figure 5:
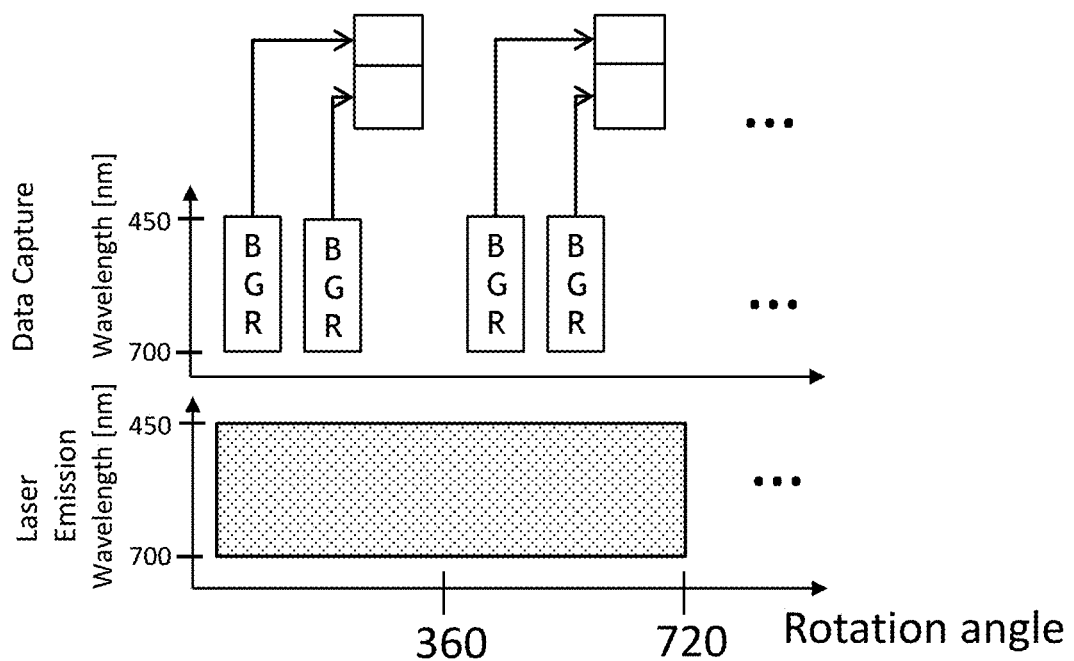
FIG. 5 is an exemplary data processing chart (top half) and timing chart (bottom half) for light where all colors are illuminated simultaneously.

Alternatively, as shown in FIG. 5, another exemplary data processing and timing chart is provided. The horizontal axis of the graph is a rotation angle of the illumination fiber, which is also correlated with time. The vertical axis is the wavelength. The bottom portion of the graph shows the laser emission of the light source. The hatched area on the bottom graph shows that the light of the broad band with wavelength range of 450 nm to 700 nm is continuously emitted and delivered to the probe. In this embodiment, the top portion of the graph of FIG. 5 shows the data from each of the red, green and blue light that can be combined into an image. Additionally, a second image can be created from the light at a separate location and stitched into a single image (e.g., with the light data from the other location) having increased effective field of view.

In some embodiments, the gratings are configured as a three-faceted pyramid. The three facet pyramid is preferably to a two 2 facet-chisel shape to avoid the 0th order diffracted light from one grating to overlap with the 1st order diffraction of the other.

Figure 6:
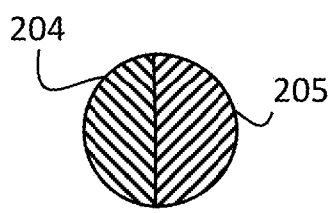
FIG. 6 is a front view of an exemplary embodiment of a probe tip.

In some embodiments, the plane of the two grating can be extended to eliminate grating surface 206, as shown in FIG. 6 (i.e., the gratings 204 and 205 are including in the embodiment of FIG. 6, whereas the grating 206 is not included). In these embodiments, two colors may be provided to distinguish blood and tissue that is not blood colored. In some other embodiments, four gratings can be used to provide four light colors instead of three.

Figure 7A:
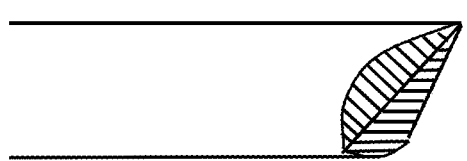
FIGS. 7(a) and 7(b).
Figure 7B:
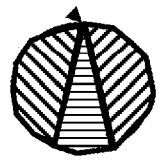

In yet other embodiments, such as when a galvo motor is used instead of a rotary junction, the fiber tip may be configured with the multiple facets at an angle such as shown in FIGS. 7(a) and 7(b) (e.g., each of the facets may be placed at different angles, slopes or tapers).

Figure 8:
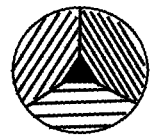
FIG. 8 is the front view of the probe tip of FIG. 2(a) with the tip removed.

In other embodiments, the tip of the grating may be removed such as shown in FIG. 8 (e.g., the tip of a three-faceted pyramid or other shaped structure may be removed).

Exemplary designs of the three gratings are summarized in Table 1A.

TABLE 1A

Grating designs of the color probe with varied pitch

| | Incident Angle [deg] | Grating lines [lines/mm] | Pitch [nm] | Long Wavelength | | Short Wavelength | |
| --- | --- | --- | --- | --- | --- | --- | --- |
| | | | | Wavelength [nm] | Diffraction angle [deg] | Wavelength [nm] | Diffraction angle [deg] |
| RED | 35 | 1710 | 584.8 | 700 | 54.7 | 599 | 44.4 |
| GREEN | 35 | 2000 | 500.0 | 598 | 54.6 | 512 | 44.4 |
| BLUE | 35 | 2339 | 427.5 | 511 | 54.6 | 438 | 44.4 |

The three gratings exemplified in Table 1A are designed for the case where the grating and the glass spacer material has a refractive index of 1.5 and the outside medium is air with a refractive index of 1.0. The incident angles of three gratings are matched for ease of fabrication. The facets are all inclined at 35 degrees from a perpendicular plane to the optical axis, and the rays entering the grating will be almost parallel to the optical axis of the probe. Thus, the incident angles to the grating will be 35 degrees. This particular embodiment is made such that the gratings vary in the pitch, such that red bandwidth of 599 nm to 700 nm, green bandwidth of 512 nm to 598 nm, and blue bandwidth of 438 nm to 511 nm will diffract at angles of 44.4 degrees to 54.6 degrees from the optical axis. The gratings may be redesigned for a specific refractive index of the glass material or for the medium of use, such as water or saline.

The two exemplary gratings in Table 1B are designed for the case where the grating and the glass spacer material has a refractive index of 1.5 and the outside medium is air with a refractive index of 1.0. The incident angles of two gratings are matched for ease of fabrication. The facets are all inclined at 35 degrees from a perpendicular plane to the optical axis, and the rays entering the grating will be almost parallel to the optical axis of the probe. Thus, the incident angles to the grating will be 35 degrees. This particular embodiment is made such that the gratings vary in the pitch, such that broad bandwidth of 450 nm to 700 nm will diffract at angles of 45.8 degrees to 85.4 degrees from the optical axis for one grating and 24.3 degrees to 45.9 degrees from the optical axis for the other grating. As the total, these two gratings will create a field of view of 61.1 degrees. The diffraction angles are slightly overlapped for the two gratings so that the two data can be stitched without any loss of image at the boundary. The gratings may be redesigned for a specific refractive index of the glass material or for the medium of use, such as water or saline.

TABLE 1B

Grating design.

| | Incident Angle [deg] | Grating lines [lines/mm] | Pitch [nm] | Long Wavelength | | Short Wavelength | |
|---|---|---|---|---|---|---|---|
| | | | | Wavelength [nm] | Diffraction angle [deg] | Wavelength [nm] | Diffraction angle [deg] |
| UP | 35 | 1500 | 666.7 | 700 | 45.9 | 450 | 24.3 |
| Down | 35 | 2330 | 429.2 | 700 | 85.4 | 450 | 45.8 |

By choosing the different grating design, pitch and incident angle as shown in Table 1A, as shown in Table 1B, or for some other design dependent on the materials and configuration, the diffraction can cover a wider illumination angle, and thus a wider field of view is obtained.

Second Embodiment

The second embodiment as exemplified herein is similar to the first embodiment in its system, but the illumination part of the probe is designed differently from the first embodiment.

Table 2A shows the embodiment of three grating designs. The grating pitches are the same for the three gratings and the incident angle, or the facet angles, of the three gratings are different.

In this exemplary embodiment, the grating used for red band illumination is at 49 degrees from the perpendicular plane of the optical axis and diffracts and illuminates the light of wavelength 595 nm to 700 nm to approximate diffraction angles of 52.3 degrees to 64.5 degrees from the optical axis. The grating used for green band illumination is at 18 degrees from the perpendicular plane of the optical axis and diffracts and illuminates the light of wavelength 513 nm to 594 nm to similar angles as the red wavelength band from the optical axis. The grating used for green band illumination is at 7 degrees from the perpendicular plane of the optical axis and diffracts and illuminates the light of wavelength 512 nm to 446 nm to similar angles as the red wavelength band from the optical axis.

TABLE 2A

Grating designs of the color probe with varied incidence angle

| | Incident Angle [deg] | Grating lines [lines/mm] | Pitch [nm] | Long Wavelength | | Short Wavelength | |
|---|---|---|---|---|---|---|---|
| | | | | Wavelength [nm] | Diffraction angle [deg] | Wavelength [nm] | Diffraction angle [deg] |
| RED | 49 | 2000 | 500.0 | 700 | 64.5 | 595 | 52.3 |
| GREEN | 18 | 2000 | 500.0 | 594 | 64.4 | 513 | 52.2 |
| BLUE | 7 | 2000 | 500.0 | 512 | 64.3 | 446 | 52.2 |

Table 2B shows another example of three grating designs. The grating pitches are the same for the three gratings and are the same as in Table 2A. The incident angles, or the facet angles, of the three gratings are different.

TABLE 2B

Grating designs of the color probe with varied incidence angle

| | Incident Angle [deg] | Grating lines [lines/mm] | Pitch [nm] | Long Wavelength | | Short Wavelength | |
|---|---|---|---|---|---|---|---|
| | | | | Wavelength [nm] | Diffraction angle [deg] | Wavelength [nm] | Diffraction angle [deg] |
| RED | 49 | 2000 | 500.0 | 700 | 64.5 | 609 | 53.9 |
| GREEN | 20.2 | 2000 | 500.0 | 608 | 64.5 | 536 | 53.8 |
| BLUE | 9.8 | 2000 | 500.0 | 535 | 64.4 | 475 | 53.8 |

Third Embodiment

Figure 9:
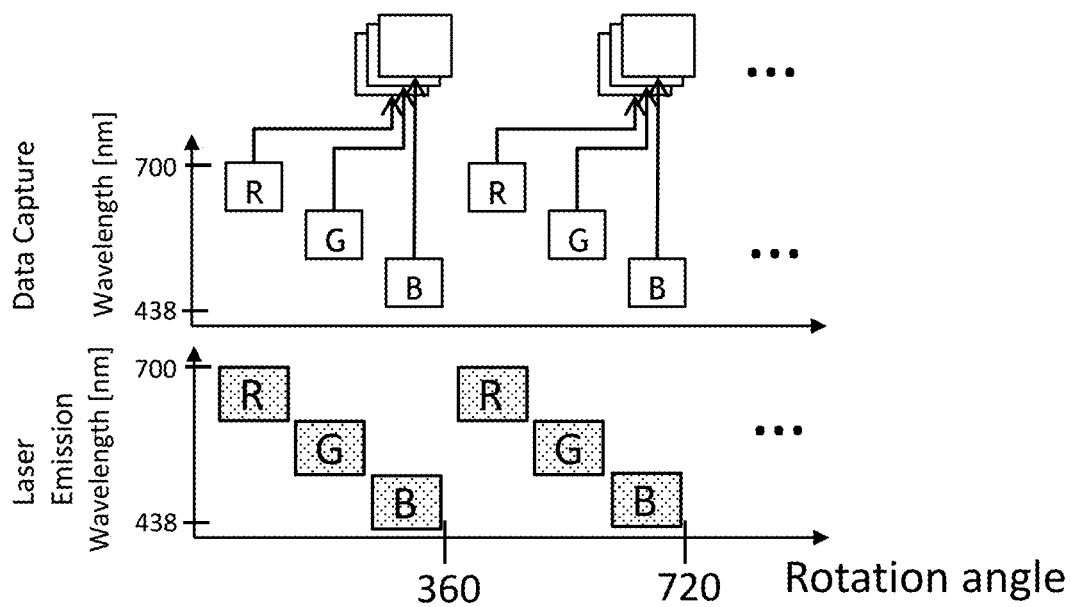
FIG. 9 is an exemplary data processing chart (top half) and timing chart (bottom half) for three colors of light.

The third embodiment uses switching of illumination to reduce total light intensity to the probe. In FIG. to, this embodiment has a switching unit (see e.g., switches SW1 604, SW2 605 and SW3 606) in between the light source for the three colors (601, 602, and 603) and the probe (not shown). The synchronization timing is shown in FIG. 9. The bottom graph shows the illumination pattern and timing and the top graph shows the data capturing. The switching of the illumination of the different bandwidths of the laser light is synchronized with the rotation of the illumination part of the probe and the data capturing from the linescan camera (e.g., such as a linescan camera 118). When the grating for delivering red light to the field of view is in position, red bandwidth light is switched on. The data from the red band pixels are used for a red color frame. When the grating for delivering green light to the field of view is in position, green bandwidth light is switched on. The data from the green band pixels are used for a green color frame. When the grating for delivering blue light to the field of view is in position, blue bandwidth light is switched on. The data from the blue band pixels are used for a blue color frame.

One particular advantage of this embodiment is that, by switched illumination of the light source, the crosstalk of the probe can be reduced.

Figure 10:
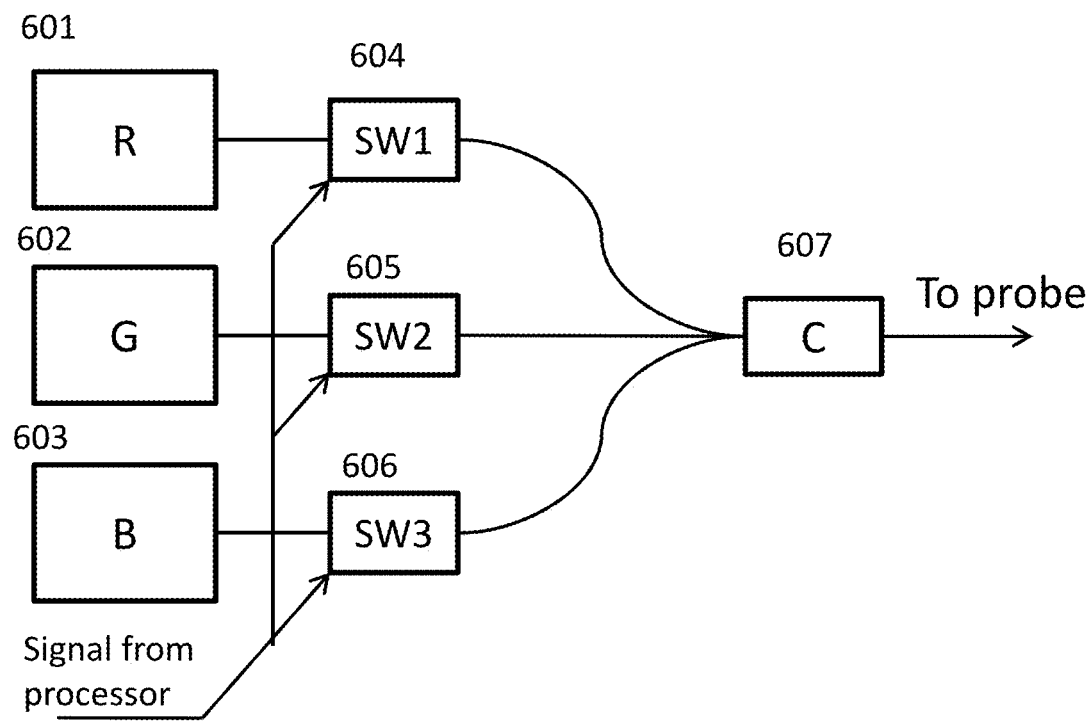
FIG. 10 is a schematic for three light colors as they propagate to the probe.

A switching mechanism on the light source is explained using FIG. 10. In this case, a light source, such as a super luminescence diode, is used for each of three wavelength bands. Super luminescence light sources 601, 602 and 603 emit red, green and blue broadband light respectively. As light is emitted by optical fiber, three fibers independently go through switches 604, 605 and 606. The switches 604, 605, 606 are actively controlled to synchronize with the rotation of the probe and data capture by a signal from a processor unit. The optical fibers from the switches 604, 605, 606 are then sent to an optical combiner 607. The fiber exiting the optical combiner 607 is connected to the probe for illumination.

Other configurations are possible using other types of optical switches and combiners, such as dichroic combiners. The same can be configured using a broad band supercontinuum laser by first dispersing the light and using mirrors or splitting the light by dichroic mirrors into three wavelength bands, and then using optical switches to turn on and off. After the optical switches, the light is collected again by a grating or dichroic mirror combiner, into one beam and then to an optical fiber for sending to the probe.

This lowers the light intensity entering the probe and irradiating the sample. Lowering the light intensity will be advantageous in terms of lifetime of the probe and safety of the user.

Fourth Embodiment

Figures 11A, 11B:
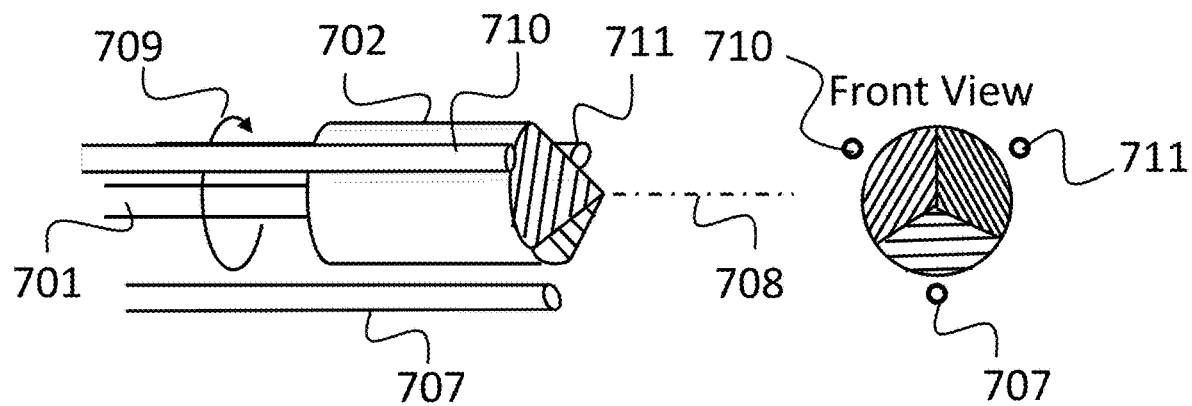
FIGS. 11(a) and 11(b).

The fourth embodiment utilizes two (2) or more detection waveguides, such as detection fibers. FIG. 11(a) shows the probe of this embodiment. The illumination part 701 and/or 702 of the probe is the same as in the first embodiment (see e.g., the single mode fiber 201 and/or the GRIN lens 202 of FIG. 2(a)). The illumination part 701, 702 are rotated with axis of rotation 708 as illustrated by the arrow 709 shown in FIG. 11(a). In FIG. 11(a), three detection fibers 707, 710 and 711 are equally spaced around the illumination fiber. The tip of the illumination fibers are angled such that each of the fibers has a specific field of view. As the single mode fiber 701 and/or the illumination part 702 is rotated around an axis of rotation 708, the illumination light irradiation pattern rotates, and the detection fibers 707, 710, 711 collect light from the respective field of view.

Figure 12:
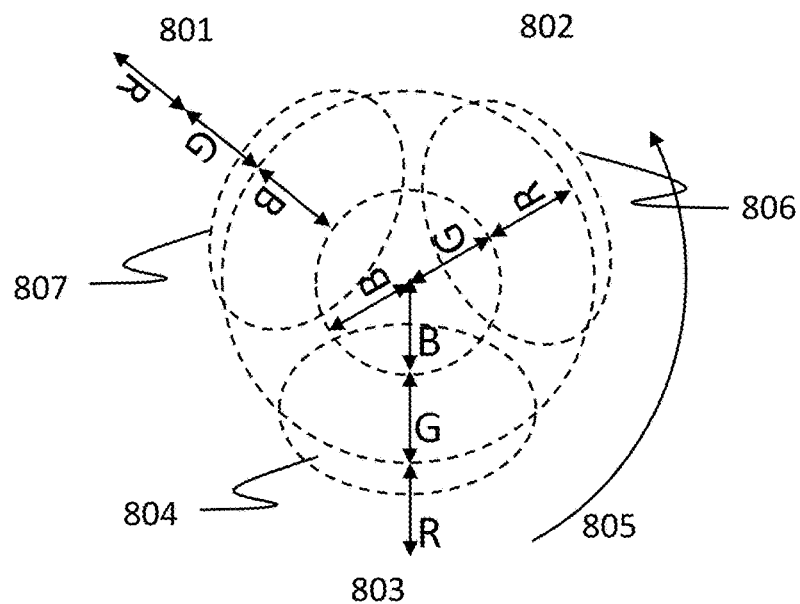
FIG. 12 is a schematic showing the illumination light pattern on a screen perpendicular to the rotation axis, observed from the direction of the probe for light from the probe shown in FIG. 11(a).

FIG. 12 shows the field of view of three detection fibers. The detection fibers 707, 710 and 711 have the field of view of 804, 806 and 807 respectively. The sets of 3 arrows, 801, 802 and 803 are the spectrally dispersed illumination light on the screen. The three detection fibers 707, 710, 711 may be processed independently with three spectrometers and three (3) linescan cameras. An alternative configuration is to have light from three detection fibers combined to create one output light and process the output light with one spectrometer having one linescan camera. A three spectrometer configuration avoids noise of the same wavelength light coming from a different fiber of a different field of view. This embodiment is advantageous to view around the internal surface of a tube or lumen, as the endoscope advances into the tube. The number of detection fibers may be increased for a more complete view around depending on the size of a field of view of each fiber.

Each detection fiber may be, for example, a single mode fiber configured in the probe to detect light from a different diffraction grating. In other embodiments, multiple fibers or multi-mode fibers may be used.

Fifth Embodiment

Figures 13A, 13B:
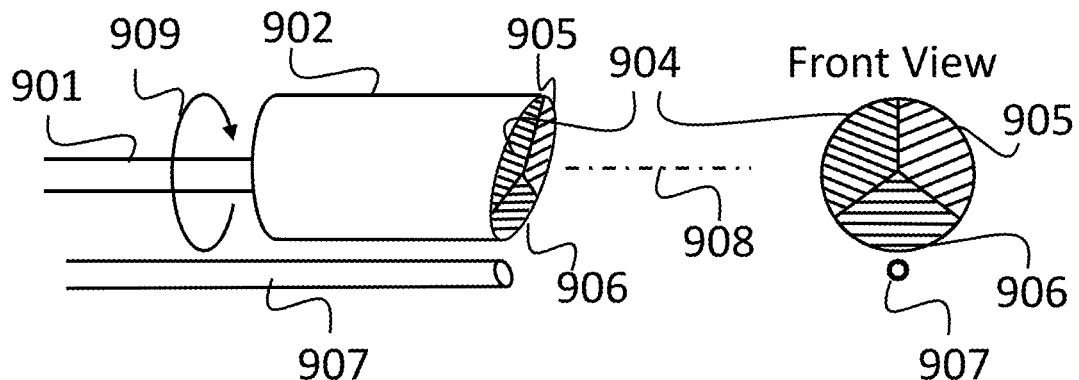
FIGS. 13(a), 13(b) and 13(c).
Figure 13C:
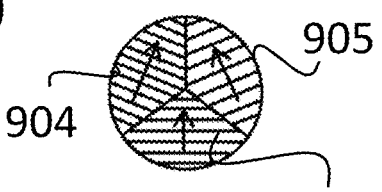

FIGS. 13(a), 13(b) and 13(c) show an embodiment of three (3) gratings on one facet. The angled facet has three (3) sectored gratings. The three (3) gratings are on the same plane but are oriented at angles to each other. The gratings may include grating vectors as shown in FIG. 13(c). As shown in FIG. 13(a), when the facet is angled tilted forward and the grating 906 is patterned with a horizontal line, the diffraction is dispersed on a vertical plane. This is because the grating vector, a vector perpendicular to the grating lines and lying on the grating plane, is on the incident plane, a plane perpendicular to the grating plane and includes the incident light vector. The diffraction rays stay on the incident plane. As for gratings 904 and 905, since the grating vector is tilted with respect to the incident plane, the diffraction light is dispersed out of the incident plane and is on a cone surface. Such orientation of diffraction is called conical diffraction. The diffraction pattern on the sample is a curve. The conical diffraction is explained in "Classical Optics and its Applications" by Masud Mansuripur, (Cambridge University Press, 2002) P. 225-229. The illumination part 901, 902 of the probe is the same as in the first embodiment (see e.g., the single mode fiber 201 and/or the GRIN lens 202 of FIG. 2(a)) with the exceptions being the aforementioned structural details of the gratings 904, 905, 906 and the shape of the illumination part 902. The illumination part 901, 902 and the gratings 904, 905, 906 are rotated with axis of rotation 908 as illustrated by the arrow 909 shown in FIG. 13(a).

Figure 14:
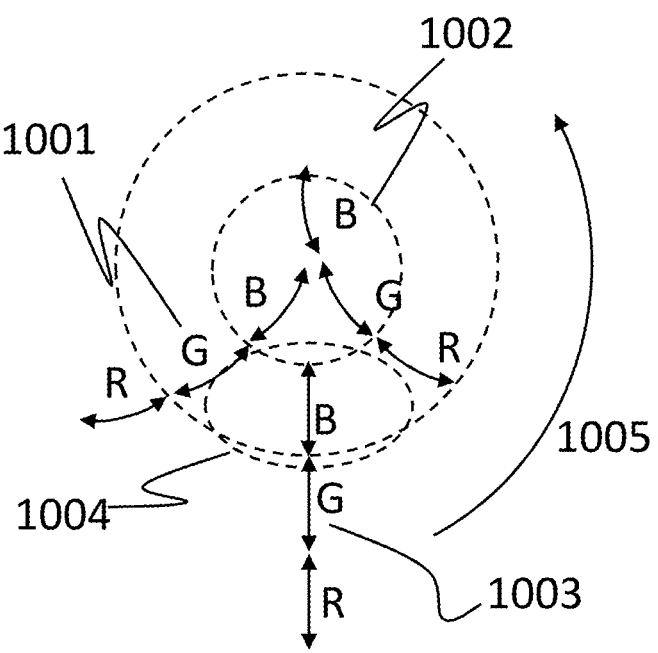
FIG. 14 is a schematic showing the illumination light pattern on a screen perpendicular to the rotation axis, observed from the direction of the probe for light from the probe shown in FIG. 13(a).

FIG. 14 shows the illumination pattern on the sample, looking at the sample from the probe. In this embodiment, the grating 906 is designed to be the densest grating and illuminates the sample with a diffraction pattern 1003. The grating lines on the gratings 904 and 905 are tilted by 5 degrees to 20 degrees with respect to the grating lines of the grating 906. The diffraction pattern from grating 904 is on a curve 1002 and the diffraction pattern from grating 905 is on a curve 1001. The movement of the illumination part is a continuous rotation as shown by the arrow 1005. The light collection by fiber 907 is the same as with the embodiments 1 and 2, and the data processing is also the same. The detection fiber 907 has a field of view of 1004. The rotation of the illumination may be a back and forth oscillation since the diffraction patterns of R of 1002, G of 1001 and B of 1003 are close together. The curve of the diffraction can be calculated as explained in the above reference and thus the image distortion caused by the curved diffraction pattern is compensated during the data process for the curved green and red color frames. FIG. 13(b) shows the area of the three gratings 904, 905, 906 to be the same. The gratings 904, 905, 906 may be changed to different size gratings to compensate for the light intensity distribution among the different color bands. For example, if the light source has less blue spectrum light, the area of the grating 9006 is made larger to increase diffracted light of blue to the line 1003.

While the conical diffraction provides a dispersed line that is curved, this embodiment having two or more diffraction lines covering different angles can be used to obtain a wider field of view than that obtained with just one grating. The curvature can be corrected using on data processing. Thus, in some embodiments there is provided a method of forming a corrected image comprising combining two or more reflected lights and correcting for curvature from the dispersion.

In some embodiments, there is provided a probe that includes a waveguide such as an optical fiber, collimating optics such as a GRIN lens, and two or more gratings oriented such that the incident plane formed by a plane perpendicular to the grating plane and the incident light are not on the same plane with each other.

Sixth Embodiment

The sixth embodiment is similar to the first embodiment in its system but the illumination part of the probe is designed differently from the first embodiment.

Table 2C shows the embodiment of two grating designs. The grating pitches are the same for the two gratings and the incident angle, or the facet angles, of the two gratings are different.

TABLE 2C

| | | | | Long Wavelength | | Short Wavelength | |
|---|---|---|---|---|---|---|---|
| | Incident Angle [deg] | Grating lines [lines/mm] | Pitch [nm] | Wavelength [nm] | Diffraction angle [deg] | Wavelength [nm] | Diffraction angle [deg] |
| UP | 52 | 2000 | 500.0 | 600 | 53.0 | 450 | 35.6 |
| Down | 18 | 2000 | 500.0 | 700 | 87.5 | 500 | 50.4 |

The grating used for one grating is at 52 degrees from the perpendicular plane of the optical axis and diffracts and illuminates the light of wavelength 450 nm to 600 nm to diffraction angles of 35.6 degrees to 53 degrees from the optical axis. The second grating used for illumination is at 18 degrees from the perpendicular plane of the optical axis and diffracts and illuminates the light of wavelength 500 nm to 700 nm to diffraction angles of 50.4 degrees to 87.5 degrees from the optical axis. Again the diffraction angles of 50 degrees to 53 degrees are overlapped to avoid stitching loss of image. The data to be used are selected for respective wavelengths for each of the illumination, synchronized with the rotation of the illumination part.

In other embodiments, two or more detection fibers may be used for respective fields of view. One detection fiber can cover the field illuminated by one grating, and the other detection fiber can cover the field of view illuminated by the other grating.

Seventh Embodiment

Figure 15A:
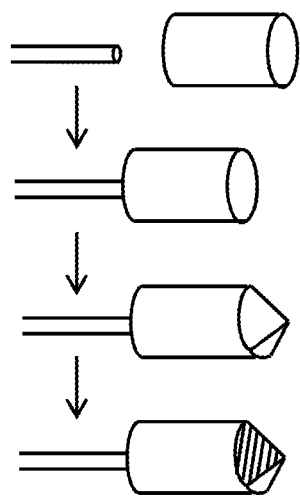
FIGS. 15(a), 15(b) and 15(c) are diagrams showing three different tip fabrications.

This embodiment provides an exemplary method of fabrication for the illumination part. FIG. 15(a) shows a schematic of fabrication steps. First the GRIN lens with an appropriate length is prepared by polishing to the correct length. The GRIN lens and the optical fiber are spliced with a splicer. The tip of GRIN lens is polished to create a pyramidal surface. This can be done using fiber end polisher. The grating is patterned on the tilted plane by stamping a curable material to each of the surface with an appropriate master grating and curing the material to form a grating, one at a time.

In some embodiments, there is provided a method of making a probe comprising the step of polishing the tip of an optical element to a pyramid shape. Then, gratings are formed on the pyramid facets. The grating may be patterned at the tip of the illumination probe by any known method such as stamping. In some embodiments, there is provided a method of making a probe comprising the step of polishing the tip of the optics to an angle, patterning a grating on the angled surface, and bundling the units at an orientation such that the multi facet shape is configured.

Eighth Embodiment

Figure 15B:
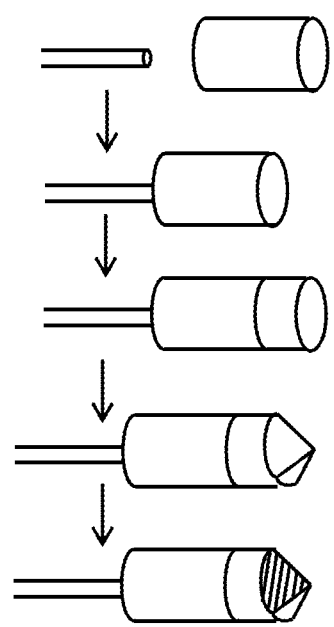
Figure 15C:
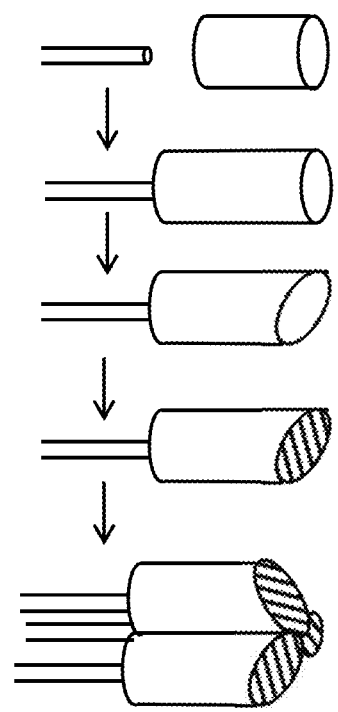

This exemplary embodiment provides another exemplary method of fabrication for the illumination part. FIG. 15(b) shows an embodiment where the multifaceted grating is made on a glass part. First the GRIN lens with an appropriate length is prepared by polishing to the correct length. The GRIN lens and the optical fiber are spliced with a splicer. Then a coreless glass rod is spliced on the GRIN lens. It may be attached with adhesives. The coreless glass rod is cleaved and polished to a specified length. The tip of the coreless glass rod is polished to create a pyramidal surface. This can be done using a fiber end polisher. The grating is patterned on the tilted plane by stamping a curable material to each of the surface with an appropriate master grating and curing the material to form a grating, one at a time.

Ninth Embodiment

In another exemplary embodiment is a multifacet illumination probe fabricated by bundling. FIG. 5(c) shows the schematics of fabrication steps. First the GRIN lens with an appropriate length is prepared by polishing to the correct length. The GRIN lens and the optical fiber are spliced with a splicer. The GRIN lens is polished at an angle. The grating is patterned on the tilted plane by stamping a curable material to the surface with an appropriate master grating and curing the material to form a grating. These steps create a fiber grating unit (also referred to as a fiber illumination unit). Three sets of the fiber grating unit are fabricated. Each of the three sets of the fiber grating unit must have appropriate angle and grating pitch for each grating of the multi facet probe. Three fiber illumination units are bundled at an appropriate orientation. The bundled set may be bonded by adhesives or a heat shrink tube.

The pyramid shape is not limited to having a vertex at the center of the diameter of the fiber illumination or grating unit. A pyramid or other shape that has its vertex at one point on the circumference of the outer circle of the cylinder of the fiber illumination or grating unit may be used. This shape can be fabricated as disclosed herein as well.

In some embodiments, the vertex can be polished off so as not to create a point on the probe where the energy of the light is collected or scattered. The polished surface may be coated with absorbing material so that the stray light is suppressed.

Tenth Embodiment

Red, green and blue color reconstruction is discussed in several of the embodiments above. However, each of these embodiments may be modified such that the three (or, in some applications, two or four) different color bands can be narrowed, broadened, or shifted as desired for the particular application. For example, it can be important for a doctor to distinguish red blood from tissue. One color band can be optimized for visualizing blood as red and other color band(s) can be spread over the remaining bandwidth. In some embodiments, one or more of the color bands may be in the infrared range. Alternatively or in addition, the color bands may extend in the Ultraviolet ("UV") range. The exemplary range of the wavelength can be typically from 400 nm to 800 nm or from 500 nm to 950 nm. In some embodiments, the full range of color is limited where the longest wavelength is less than twice the shortest wavelength.

Additional Embodiment

Figure 16A:
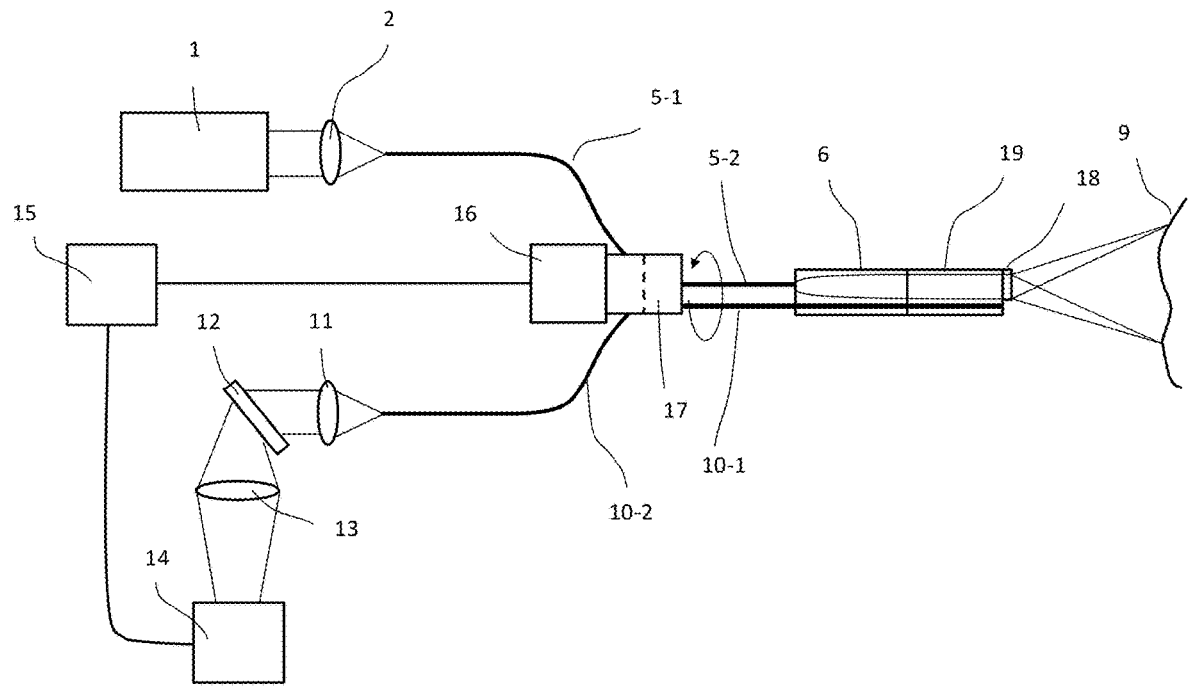
FIG. 16(a) is a basic configuration example of an embodiment.

The basic configuration of an embodiment will be described with reference to FIG. 16(a). Light flux emitted from a light source 1 is white light having a wide band, and is cast into an illumination light fiber 5-1 by a coupling lens 2. The illumination light fiber 5-1 is linked to an illumination light fiber 5-2 connected to a later-described probe optical system, by a rotary joint 17 attached to a one-way rotational motor 16. The probe optical system performs one-way rotational action by the one-way rotational motor 16. The probe optical system has an illumination unit that is configured including a gradient-index lens (generally referred to as a "GRIN lens") 6, a beam splitter optical system 19, and a diffractive grating 18. The GRIN lens 6 converts light emitted from the illumination light fiber 5-2 into convergent light at the position of a subject 9 to be observed. The convergent light passes through the beam splitter optical system 19 and is cast into the diffractive grating 18 attached to the tip of the beam splitter optical system 19. The incident light is emoted or emitted at a predetermined diffraction angle due to the diffraction effect, and illuminates the subject 9. The diffraction angle changes dependent on wavelength in accordance with the nature of the diffractive grating, so which position of the subject 9 is to be illuminated changes in accordance with the wavelength. In other words, the wavelength and illuminance position correspond in a one-to-one relationship.

The light reflected at the subject 9 is cast or emitted into the diffractive grating 18 again, and is diffracted in the direction of the beam splitter optical system 19. The diffracted light is cast or emitted into a detection fiber 10-1. The detection fiber 10-1 also is connected to the rotary joint 17, and linked to a detection fiber 10-2. The emission end of the detection fiber 10-2 is connected to a spectral unit. In at least one embodiment, the spectral unit is configured to include a collimator 11, a diffraction grating 12, an imaging lens 13, and a line sensor 14. The light emitted from the detection fiber 10-2 is guided to the collimator 11, becomes parallel light, and is input to the diffraction grating 12. The diffraction angle changes dependent on the wavelength, in the same way as the operation of the diffractive grating 18 in the probe optical system, so the detection light is emitted from the diffraction grating 12 at different diffraction angles in accordance with the wavelength component thereof. The emitted light is guided to a sensor face of the line sensor 14 by the imaging lens 13. Which position on the sensor face the light reaches changes in accordance with the wavelength, so the spectrum of the detected light (spectral distribution) can be measured by measuring the one-dimensional intensity distribution. The spectral data is output to a data processor 15. The data processor 15 is connected to a control unit of the one-way rotational motor 16, and stores the above spectral data along with time t and rotation angle of the one-way rotational motor 16 in memory.

As described above, the illuminance position of the subject illumination light and the wavelength correspond in a one-to-one relationship, so the above spectrum is represented, or indicated, by the intensity distribution of reflected light in accordance with the subject position. This intensity distribution of reflected light is only a one-dimensional distribution since the diffractive grating 18 is a one-dimensional diffractive grating, but sub-scanning in another dimension is performed by the one-way rotational motor 16, so the intensity distribution can be made two-dimensional in one or more embodiments. That is to say, a subject image can be obtained by performing image-forming processing based on the relationship between the intensity distribution of the reflected light, time t, and rotation angle of the one-way rotational motor 16, so the present system can be used as an endoscopy system.

Figure 16B:
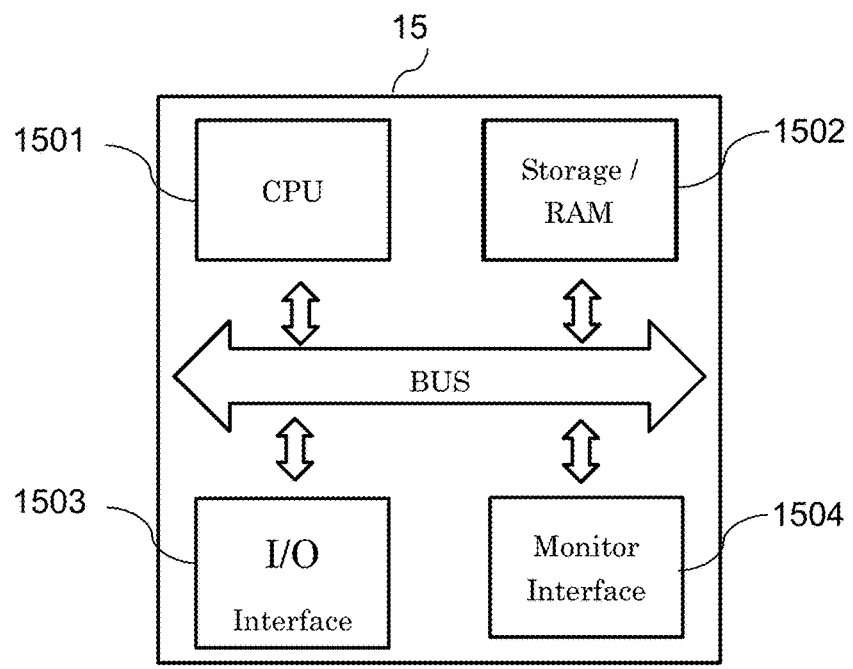
FIG. 16(b) is an exemplary configuration of a data processor.

The details of the data processor 15 are shown in FIG. 16(*b*). A data processor or computer system 15 includes a CPU 1501, storage/RAM 1502, an I/O interface 1503, and a monitor interface 1504. Also, the data processor 15 may comprise one or more devices. For example, one computer may include the components 150, 1502, and 1503, and another computer may include the component 1504. The subject teachings relating to the data processor 15 may be used for the processor 122 as shown in FIG. 1, and may include one or more components of the data processor 15 in the processor 122.

The CPU 1501 is configured to read and perform computer-executable instructions stored in the storage/RAM 1502. The computer-executable instructions may include those for the performance of the methods and/or calculations described herein.

The storage/RAM 1502 includes one or more computer readable and/or writable media, and may include, for example, a magnetic disk (e.g., a hard disk), an optical disc (e.g., a DVD or a Blu-ray), a magneto-optical disk, semiconductor memory (e.g., a non-volatile memory card, flash memory, a solid state drive, SRAM, DRAM), an EPROM, an EEPROM, etc. The storage/RAM 1502 may store computer-readable data and/or computer-executable instructions. Each of the components in the computer system 15 communicates with each other via a bus. For example, the spectrum data from the line sensor 14 is stored in the storage/RAM 1502.

The I/O interface 1503 provides communication interfaces to input and output devices, which may include the line sensor 14, a one-way rotational motor 16, a light source 1, the user interface unit (UIF) and a communication cable and a network (either wired or wireless). The user interface unit UIF may include a keyboard, a mouse, a touch screen, a light pen, a microphone, and so on. The monitor interface 1504 provides display images to a monitor.

The diffractive grating 18 will be described in detail. A two-dimensional diffractive grating 18 that can also generate diffracted light in a direction away from the plane of the drawings is used in the present embodiment. FIG. 17 is a schematic diagram viewing the two-dimensional diffractive grating 18 from the front. The solid lines in FIG. 17 that are drawn at narrow intervals represent the grating pattern of the diffractive grating. A feature of the diffractive grating 18 is that the diffractive grating patterns differ in each of three areas 18-1, 18-2, and 18-3, into which the diffractive grating 18 has been divided. The difference in diffractive grating patterns leads to generating variations in diffraction direction and diffraction wavelength of light, which will be described later. The following is a description of generating such variation.

FIG. 18 is a diagram illustrating a distribution of illumination light illuminating the subject 9, as viewed from the front. The illumination light has three focal point spectrums maintaining a 120 degree relative angle from each other, as illustrated in FIG. 18. The focal point spectrum denoted by 20-1 in FIG. 18 is formed by light diffracted in area 18-1 of the diffractive grating 18 in FIG. 17. In the same way, the focal point spectrum 20-2 is formed by light diffracted in area 18-2, and the focal point spectrum 20-3 is formed by light diffracted in area 18-3. That is to say, unlike a conventional color endoscope, the diffractive grating 18 is configured to generate diffracted light in three different directions. FIG. 19 is a perspective view illustrating the relationship between the diffractive grating 18 and the three focal point spectrums 20-1, 20-2, 20-3. It can be seen here that the intersection point of the three focal point spectrums 20-1, 20-2, 20-3 is situated in the rotational axis of the probe, indicated by a single-dot dashed line in FIG. 19.

Function of Beam Splitter Optical System

Figure 24:
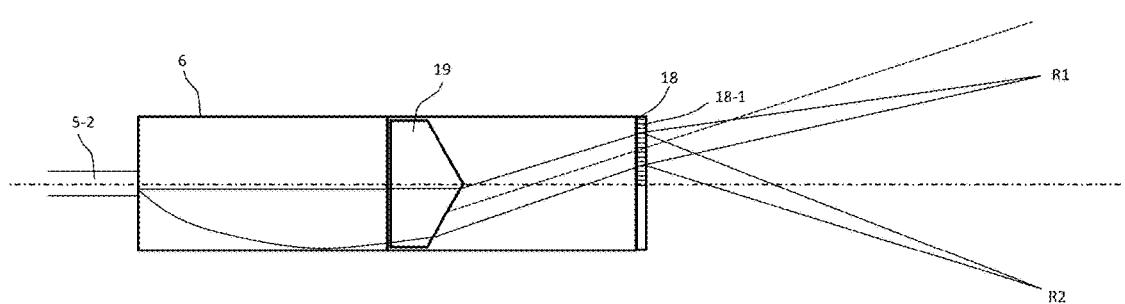
FIG. 24 illustrates placement of optical system elements for separation of diffracted light.

Now, it is effective to use first-order diffraction light for the diffracted light used as illumination light, from the point of efficiency. The present embodiment is arranged with the diffractive grating inclined to avoid 0th-order diffraction light from being projected on the subject (e.g., such as the subject 9), and arranged so that the area where 0th-order diffraction light reaches does not overlap with the subject (e.g., such as the subject 9). FIG. 24 is an explanatory diagram of such an arrangement, and is a cross-sectional diagram including the rotational axis of the probe (single-dot dashed line in FIG. 24) and the focal point spectrum 20-1. Light emitted from the illumination light fiber 5-2 is converted by the GRIN lens 6 into a beam that converges near the subject (e.g., such as the subject 9). Although FIG. 24 only illustrates rays at the lower half side to facilitate understanding, the beam distribution actually is axis-symmetric.

Figure 20:
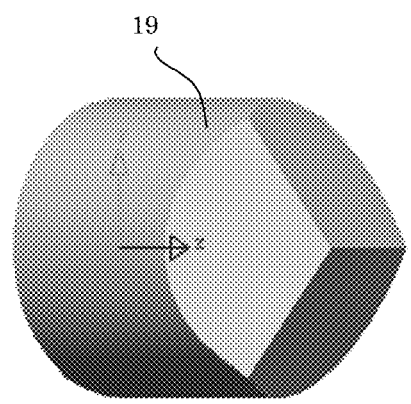
FIG. 20 is a perspective view of a beam splitter optical system.
Figure 21:
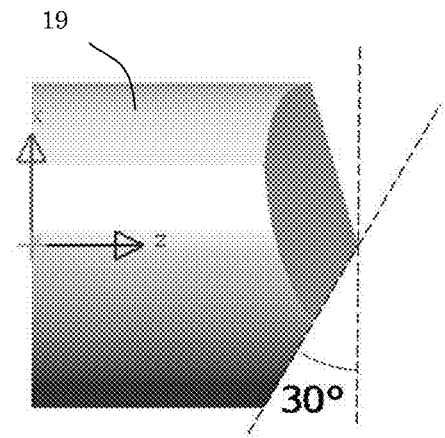
FIG. 21 is a plan view of a beam splitter optical system.
Figure 22:
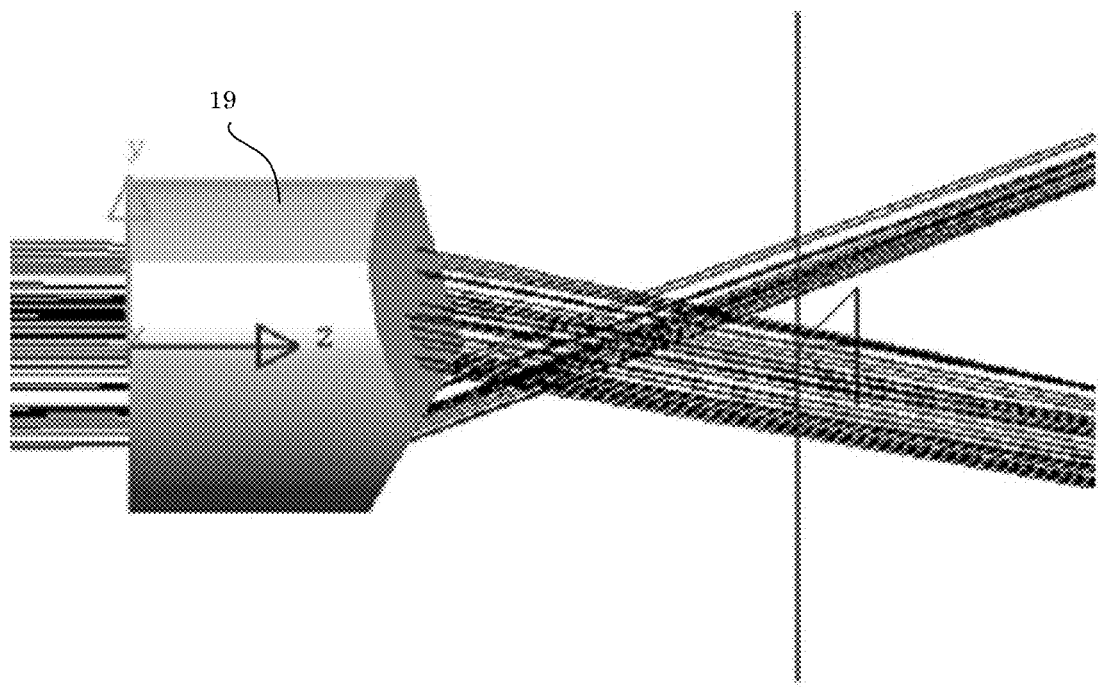
FIG. 22 illustrates the way in which rays pass through a beam splitter optical system.
Figure 23:
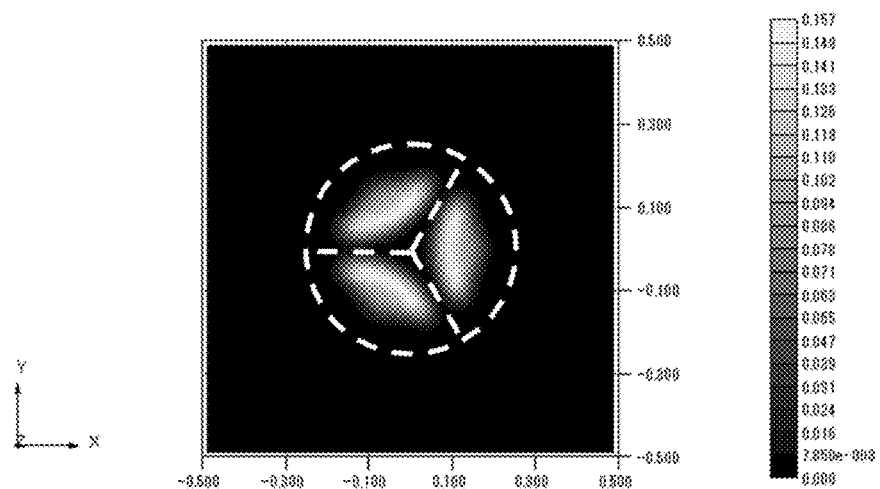
FIG. 23 illustrates an illuminance distribution on a face of the diffraction grating, formed by the light flux emitted from the beam splitter optical system.

The light emitted from the GRIN lens 6 is cast into the beam splitter optical system 19. FIG. 20 is a perspective view of the beam splitter optical system 19, and FIG. 21 is a plan view of the beam splitter optical system 19. It can be seen from FIGS. 20 and 21 that the emission side end face of the optical system includes a vertex on the z axis, and is configured including three planes inclined by 30 degrees from a plane orthogonal to the z axis in the 1 o'clock, 5 o'clock, and 9 o'clock directions. According to this configuration, in a case where parallel light is input from the end face at the opposite side, the incident beam is split in the three different directions corresponding to the three inclined faces and emitted as split beams, as illustrated in FIG. 22. FIG. 23 illustrates an illuminance distribution formed by the light flux emitted from the beam splitter optical system 19 on the diffractive grating 18. The dotted/dashed lines in FIG. 23 represent the outer shape of the diffractive grating 18 and the boundaries of the area divisions. It can be clearly seen from FIG. 23 that the original incident beam is split by the beam splitter optical system 19 so as to not overlap the three areas of the diffractive grating 18, and thus is input.

FIG. 24 illustrates the way in which the obliquely incident light to the area 18-1 of the diffractive grating is diffracted in the R1 and R2 directions, in accordance with wavelength, to form the focal point spectrum 20-1. It can be clearly seen that the directions of the focal point spectrum 20-1 and the 0th-order diffraction light (indicated by dotted line) are separated. Thus, unwanted light can be eliminated, and the subject (e.g., such as the subject 9) can be illuminated with the most efficient illumination conditions. This arrangement is made in the same way in the area 18-2 and the area 18-3, so the same illumination state is achieved in the focal point spectrum 20-2 and the focal point spectrum 20-3 as well.

Figures 25, 26:
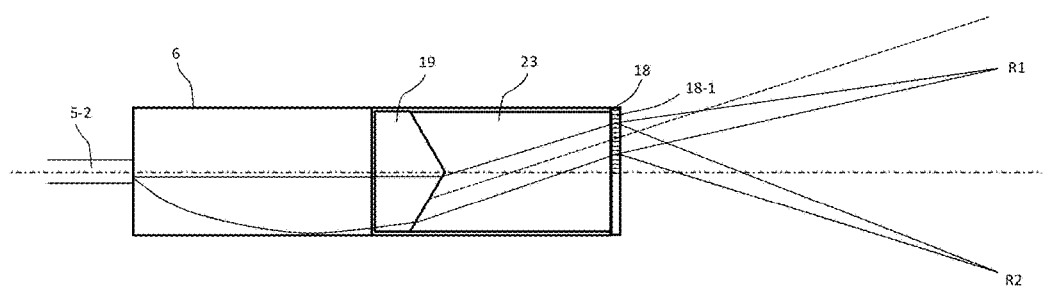
FIG. 25 illustrates placement of optical system elements for separation of diffracted light (integrated configuration).
FIG. 26 illustrates an example of glass material selection to realize an integrated probe.

Now, in a case of providing such a beam splitter optical system 19, an air gap occurs between the beam splitter optical system 19 and the diffractive grating 18, requiring a separate base for forming the diffractive grating 18. This sort of configuration readily exhibits positional misalignment among parts, and the probe is more difficult to assemble. Accordingly, a configuration such as illustrated in FIG. 25, where the air gap portion is filled in with a base material 23 of low-refractive-index glass, so as to integrate from the GRIN lens 6 through the diffractive grating 18, is effective. The incident side of the base material 23 has the same shape as the emitting side of the beam splitter optical system 19, and the air gap can be eliminated by adhesion. Further, the emitting side of the base material 23 is a plane, serving as an area where the diffractive grating 18 is formed. FIG. 26 illustrates combination examples of glass material for the base material 23 and the beam splitter optical system 19. SNPH2 (having a refractive index of 1.936) manufactured by Ohara Corporation is used as the high-refractive-index glass for the beam splitter optical system 19, and SFSL5 (refractive index of 1.49) manufactured by Ohara Corporation is used as the low-refractive-index glass for the diffractive grating 18. Accordingly, refractive power is generated at the interface between the two, and the above-described beam splitting can be realized.

Spectral Distribution of the Three Focal Point Spectrums

Figure 27:
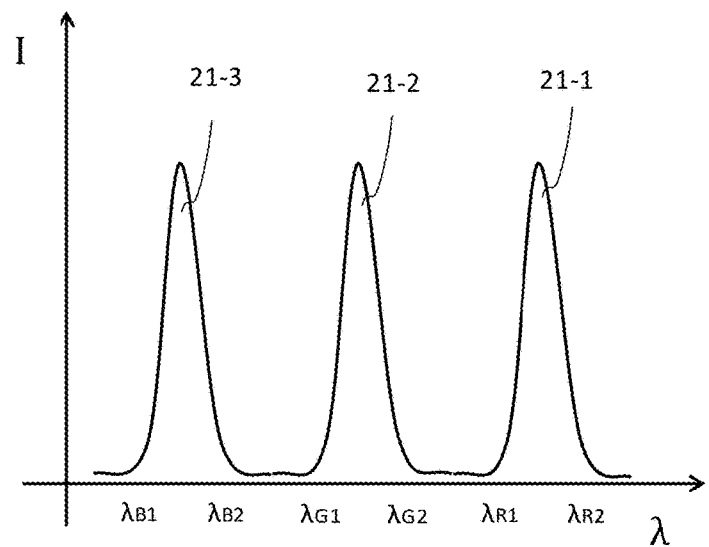
FIG. 27 illustrates spectral distribution of illumination light on a plane of a subject.

A further feature of the illumination light is that the spectral distribution is different for each of the three focal point spectrums. FIG. 27 illustrates the spectral distribution of the illumination light. The distribution denoted by 21-1 in FIG. 27 is the spectral distribution of the focal point spectrum 20-1. In the same way, the distribution denoted by 21-2 is the spectral distribution of the focal point spectrum 20-2, and the distribution denoted by 21-3 is the spectral distribution of the focal point spectrum 20-3. These each have a spectral distribution separate in accordance with the three primary colors of red (R), green (G), and blue (B), and there is substantially no frequency band overlapping among the three.

In order for illumination light having the spectral distribution such as illustrated in FIG. 27 to be projected on a desired subject area, the diffractive grating pitch d is designed so as to satisfy a later-described grating equation (2). However, in practice, the wavelength of the illumination light is distributed over a broad range, so the illumination light is projected in a focal point spectrum state outside of the desired subject area as well. If returning light from the subject (such as the subject 9), illuminated by such unwanted light, is input to the detection fiber 10-1, the subject information reconstruction may not work as intended. Accordingly, there is a need to improvise to eliminate such unwanted light.

Figure 28:
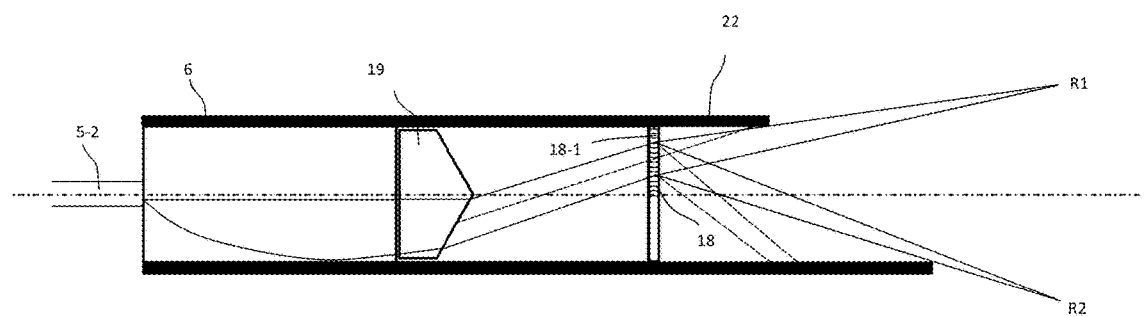
FIG. 28 illustrates a configuration for removing unwanted light.
Figure 29:
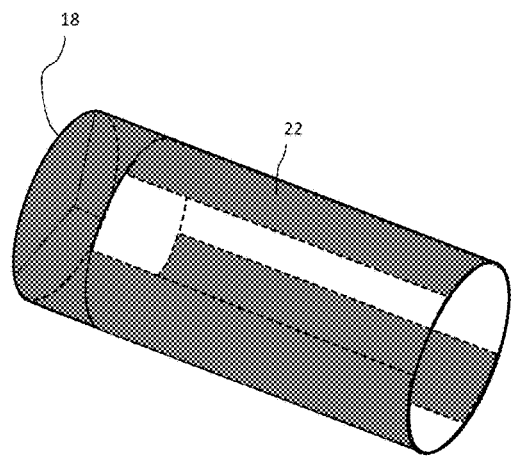
FIG. 29 is a perspective view of a light-shielding barrel.
Figure 30:
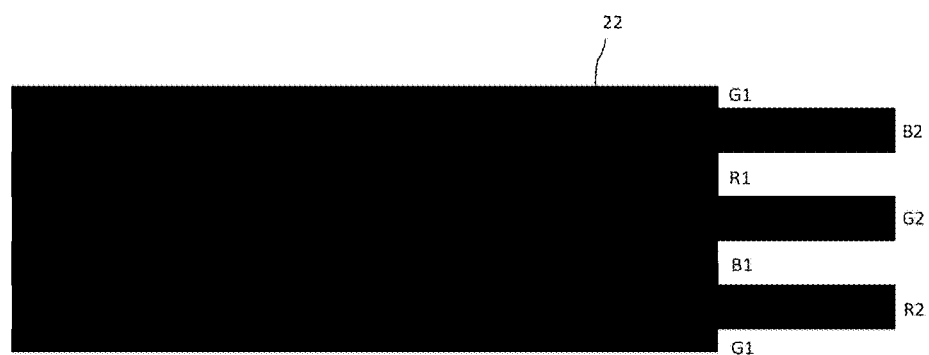
FIG. 30 is an opened-up view of the light-shielding barrel (in case where output shape is cut).
Figure 31:
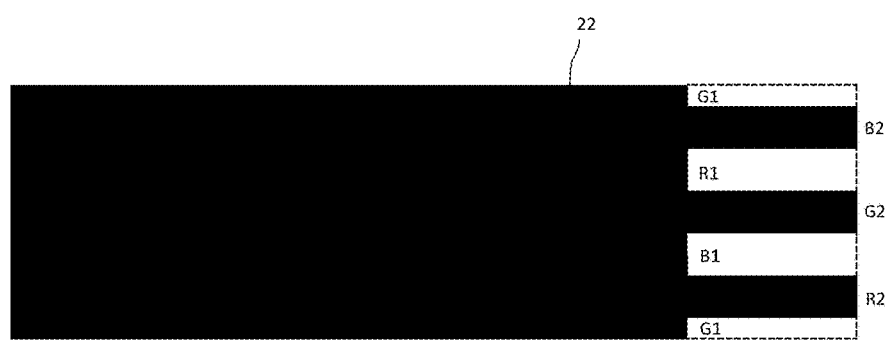
FIG. 31 is an opened-up view of the light-shielding barrel (in case where pattern-coated).

FIG. 28 illustrates an example of a configuration to eliminate the above unwanted light, by adding a part. Reference numeral 22 in FIG. 28 denotes a barrel 22 that is a cylinder formed of a light-shielding material and accommodated so as to cover the GRIN lens 6 and the beam splitter optical system 19. A feature of this part is that the barrel 22 is longer in the axial direction than the combined length of the GRIN lens 6 and the beam splitter optical system 19, and protrudes outward beyond the plane where the diffractive grating 18 is disposed. Further, light shielding material is provided with a short length at a short-wavelength (R1) side, and light shielding material is provided with a long length at a long-wavelength (R2) side. This configuration causes the subject area where the beams illuminate to be symmetrical as to the optical axis illustrated in FIG. 28 by the single-dot dashed line. The asymmetry of the light shielding material preferably holds for all three diffracted lights diffracted in the three areas of the diffractive grating 18, so in the present embodiment, the length where the light shielding material (gray regions in FIG. 29) protrude beyond the diffractive grating 18 are configured every 120 degrees in the circumferential direction, as illustrated in FIG. 29. FIG. 30 is an opened-up view of the light-shielding barrel 22. The symbols G1, R1, B1, and so on in FIG. 30 indicate the wavelength of the illumination light passing through the respective areas. Since a complex cutout of light shielding material might make manufacturing more difficult, a method may be employed such as illustrated in FIG. 31, where the barrel 22 is configured using a transmitting material having the outer shape indicated by dotted or dashed lines, and the light shielding portions are formed by pattern coating with a light shielding paint. This configuration restricts illumination light emitted from the diffractive grating 18 to a range defined by the light-shielding barrel 22, so unnecessary light can be eliminated.

One-Way Rotational Action

The one-way rotational motor 16 is used in the present embodiment to perform one-way rotational action of the probe optical system. Accordingly, the rotary joint 17, which is a mechanical part of which one end is fixed and the other rotates, is used to keep the two types of optical fibers 5 (e.g., the fibers 5-1, 5-2) and 10 (e.g., the fibers 10-1, 10-2), for illumination and detection, from becoming tangled due to rotation.

Procedures to Acquire Full-Color Images

The present embodiment enables color image acquisition, which was heretofore unachievable with conventional color endoscopes, using the features described above. The way in which this is realized is described below.

Figure 32:
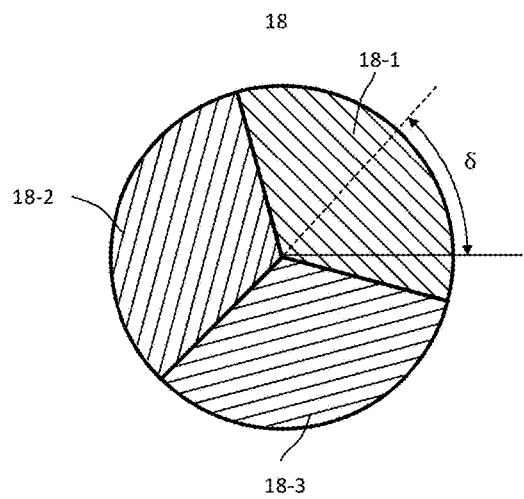
FIG. 32 is an enlarged frontal diagram of a diffraction grating when the probe optical system is rotated by δ.
Figure 33:
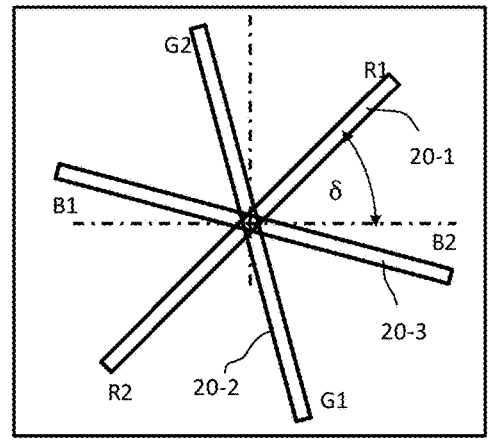
FIG. 33 is an illumination light distribution on a plane of a subject when the probe optical system is rotated by δ.
Figure 34:
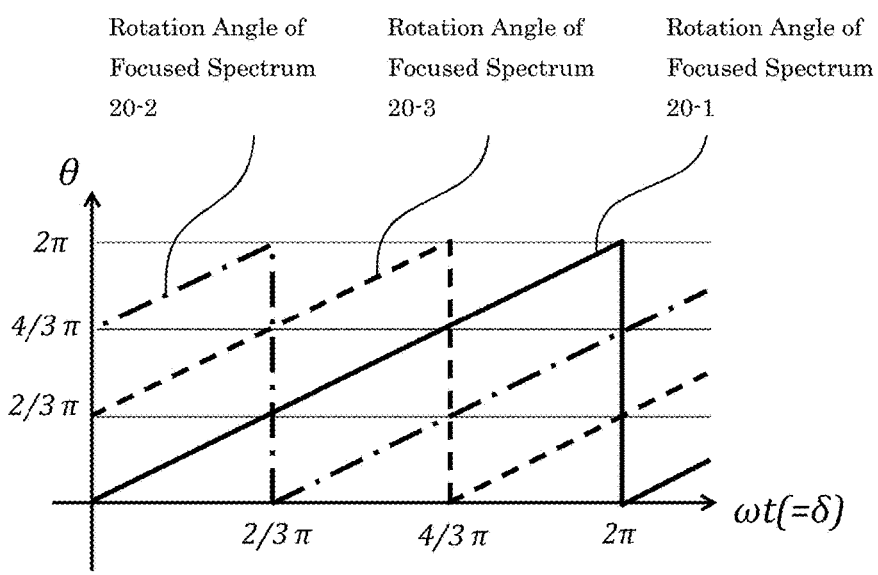
FIG. 34 is a diagram illustrating rotation angles of a focal point spectrum on a plane of a subject.

FIG. 32 is an enlarged frontal diagram of the diffraction grating 18 when the probe optical system is rotated in the counter-clockwise direction by δ. Light diffracted by the diffractive grating 18 in the state illustrated in FIG. 20 exhibits a spatial distribution rotated by the same amount δ as the rotational angle of the probe optical system, from the state in FIG. 18, as illustrated in FIG. 33. FIG. 34 is a graph illustrating time-sequence characteristics of the rotational angle of the focal point spectrum on the plane of the subject (such as the subject 9). The horizontal axis of the graph is the product ωt of the angular speed and time, this value being equal to the above rotational angle δ. The rotational angle of the focal point spectrum 20-1 illustrated by solid lines has change characteristics of exactly the same phase as the rotational angle δ. Note however, that the graph is wrapped every 2π to return the rotational angle to 0, since the graph is expressing rotational action. On the other hand, the rotational angle of the focal point spectrum 20-2 exhibiting illumination light in the green region has a phase delay of $2/3\pi$ as to the focal point spectrum 20-1 in the rotational action, and the rotational angle of the focal point spectrum 20-3 exhibiting illumination light in the blue region has a phase delay of $4/3\pi$ as to the focal point spectrum 20-1. That is to say, at any point in time, the phases of areas illuminated by the respective focal point spectrums are shifted.

Figure 35:
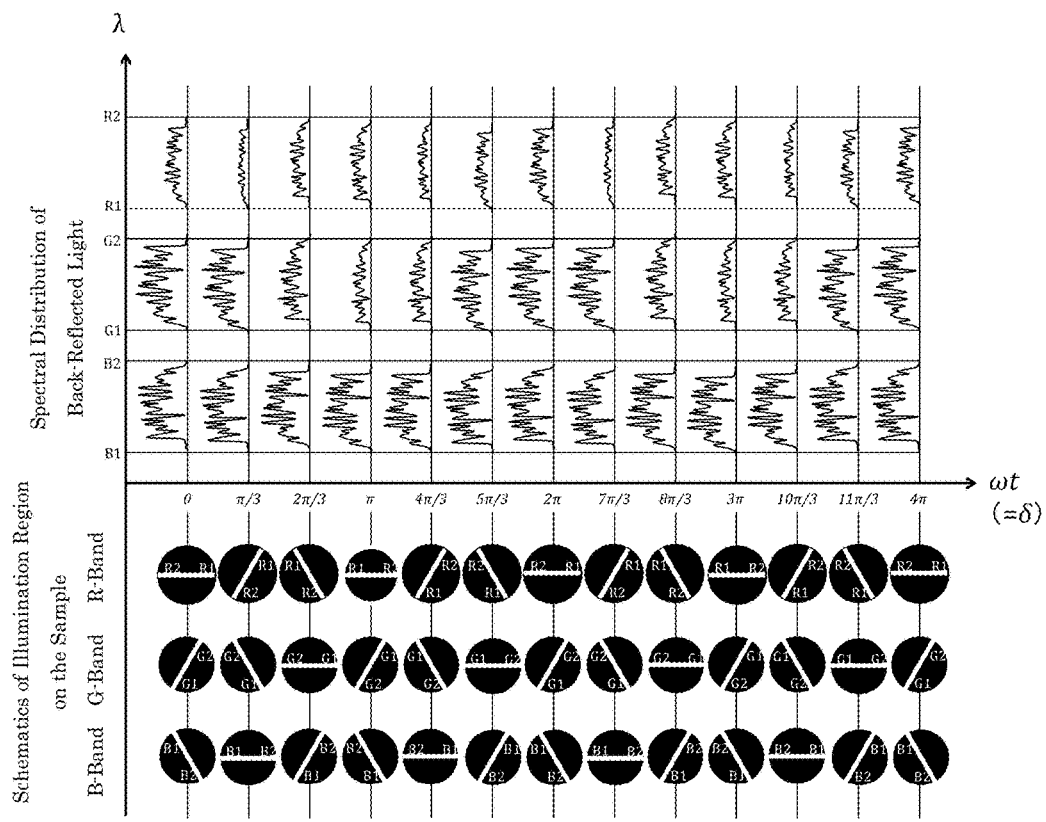
FIG. 35 is a schematic diagram of spectral distribution of returning light and change in an illuminate region on a subject.

FIG. 35 is a graph schematically illustrating subject illumination regions and time-sequence change of the spectral distribution of returning light. The horizontal axis of the graph is the product ωt (i.e., δ) of the angular speed and time, the same as in FIG. 34. The lower half of the graph illustrates time-sequence change of the subject illumination region, using frontal images of the illumination region. The black circles regions represent the subject region in FIG. 35, and the white lines represent the linear illumination light of each of R, G, and B. It can be seen here that the linear illumination lights rotate while maintaining the phase shift of 2π/3 from each other. The upper half of the graph represents the spectral distribution of returning light from the subject (such as the subject 9), detected via the detection fibers 10 (e.g., the fibers 10-1, 10-2). The vertical axis of the graph represents wavelength, indicating, in order of length of wavelength, that spectral distribution in the range of R2 to R1 is obtained as the returning light for the R illumination light, that spectral distribution in the range of G2 to G1 is obtained as the returning light for the G illumination light, and that spectral distribution in the range of B2 to B1 is obtained as the returning light for the B illumination light.

The wavelength ranges of each of the illumination lights do not overlap, so back analysis will tell which illumination light the returning light is from, simply by acquiring the spectral distribution. The spectral distributions correspond to the illumination region change of linear illumination light at the lower half of the graph, and are spectral distributions of the region illuminated by linear illumination light of different angles at each point in time. Accordingly, the spectral distribution of the entire region is completed every rotation by angle 2π, but the regions where the three linear illumination lights are illuminating have phase shift of 2π/3 as described above, which is taken into consideration when reconstructing the image data from the acquired data using the data processor 15.

Data acquisition will be described in further detail. When focusing on a certain point $P(r_p, \theta)$, an assumption will be made that this point is irradiated by a certain wavelength λRp within the focal point spectrum 20-1, and the returning light from the subject (such as the subject 9) is acquired by the CPU 1501. With this timing as t(0), the CPU 1501 calculates the subject information (subject color information) using the returning light acquired at the timing of the focal point spectrum rotating (π/3), (2π/3), (4π/3), and (5π/3). An example of combinations of the returning light being acquired regarding which wavelength at which timing, is illustrated in the table below. The CPU 1501 correlates the phase difference (or information equivalent to phase difference) as to the reference (t(0)) with the value of the detected returning lights of each wavelength, and stores the information (phase difference (or information equivalent to phase difference) with the correlated value of the detected returning lights of each wavelength) in the storage/RAM 1502. The CPU 1501 reads out combinations such as in the follow table again from the memory (such as the storage/RAM 1502), based on the phase difference correlated with the values of each returning light. The phase difference of the returning light of each wavelength from the reference is as illustrated in FIG. 35. The CPU 1501 correlates the relationship of phase differences illustrated in FIG. 35 with the values of the returning lights, and stores the information in the storage/RAM 1502.

| T | t(o) | T(π/3) | t(2π/3) | t(π) | t(4π/3) | t(5π/3) |
|---|---|---|---|---|---|---|
| λ | λRp | λBp | λGp | λRp' | λBp' | λRGp' |

Figure 36:
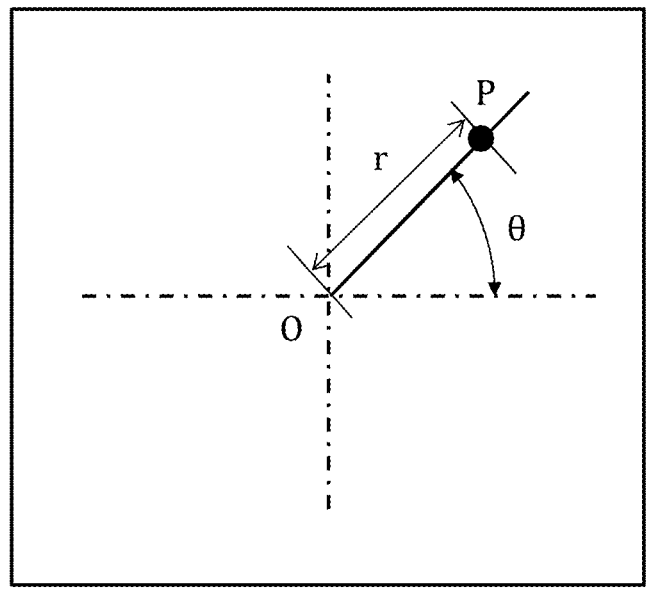
FIG. 36 illustrates setting polar coordinates on a plane of a subject.

The temporal change of illumination light distribution is rotationally symmetric as described above, so it is easier to express what point on the subject 9 is to be illuminated using a polar coordinate system as compared to an orthogonal coordinate system. Accordingly, the point P on the subject 9 is represented by polar coordinates (r, θ) in the present embodiment, as illustrated in FIG. 36. The (r-s) in FIG. 36 is the distance from the rotational symmetry point O of illumination light distribution to the point P, where s represents the difference between the center of the diffractive grating and the center of the rotational axis of the probe. In the three focal point spectrums, this r and the wavelength are uniquely associated. In a case where the value of r or the value of f (distance f is the distance from the diffractive grating 18 to the subject (such as the subject 9) as discussed below) is sufficiently larger than the value of s, there is substantially no problem in deeming (r-s) to be r, and the following description will be made with this understanding.

Figure 37:
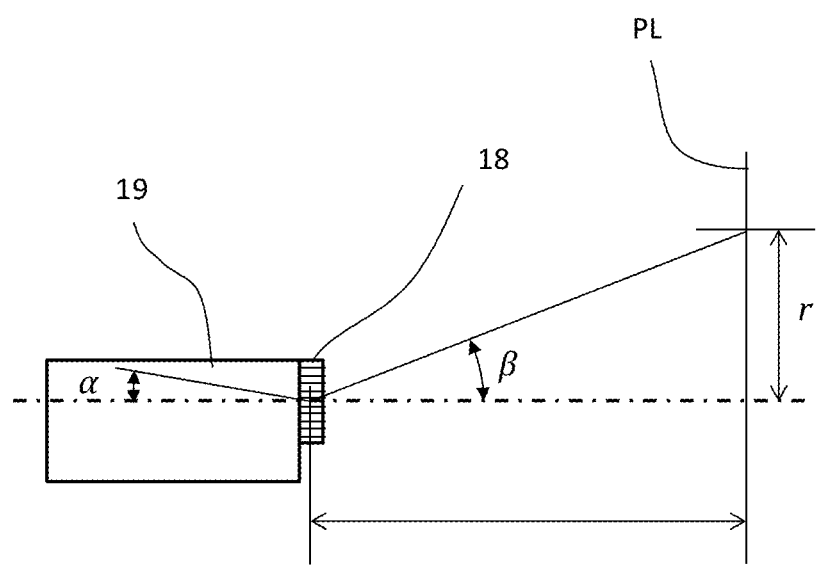
FIG. 37 illustrates the relationship between diffracted light and r.

FIG. 37 is a diagram to describe this. Diffraction angle β can be expressed as $$\sin\beta = \sin\alpha - \frac{\lambda}{d} \quad (1)$$

where α represents the incident angle of incident light to the diffractive grating 18, d represents the grating pitch of the diffractive grating 18, and λ represents the wavelength of the incident light. This is a relational expression called the grating equation. Here, r is expressed by the expression $$r = f * \tan\left(\sin^{-1}\left(\sin\alpha - \frac{\lambda}{d}\right)\right) \quad (2)$$

according to trigonometric relational expression.

That is to say, in a case where the distance f from the diffractive grating 18 to the subject (such as the subject 9), the incident angle α of the incident light, and the diffractive grating pitch d are fixed, r is uniquely determined by the wavelength λ. The CPU 1501 will determine two wavelengths corresponding to a positive r and a negative r which each have the same absolute value, these two wavelengths corresponding to λRp and λRp' in the above table. The CPU 1501 identifies the two wavelengths for various r values for each focal point spectrum. The method for identifying the two wavelengths is the same in a case of handling (r-s) as well, so a detailed description thereof will be omitted.

Figures 38A, 38B, 38C:
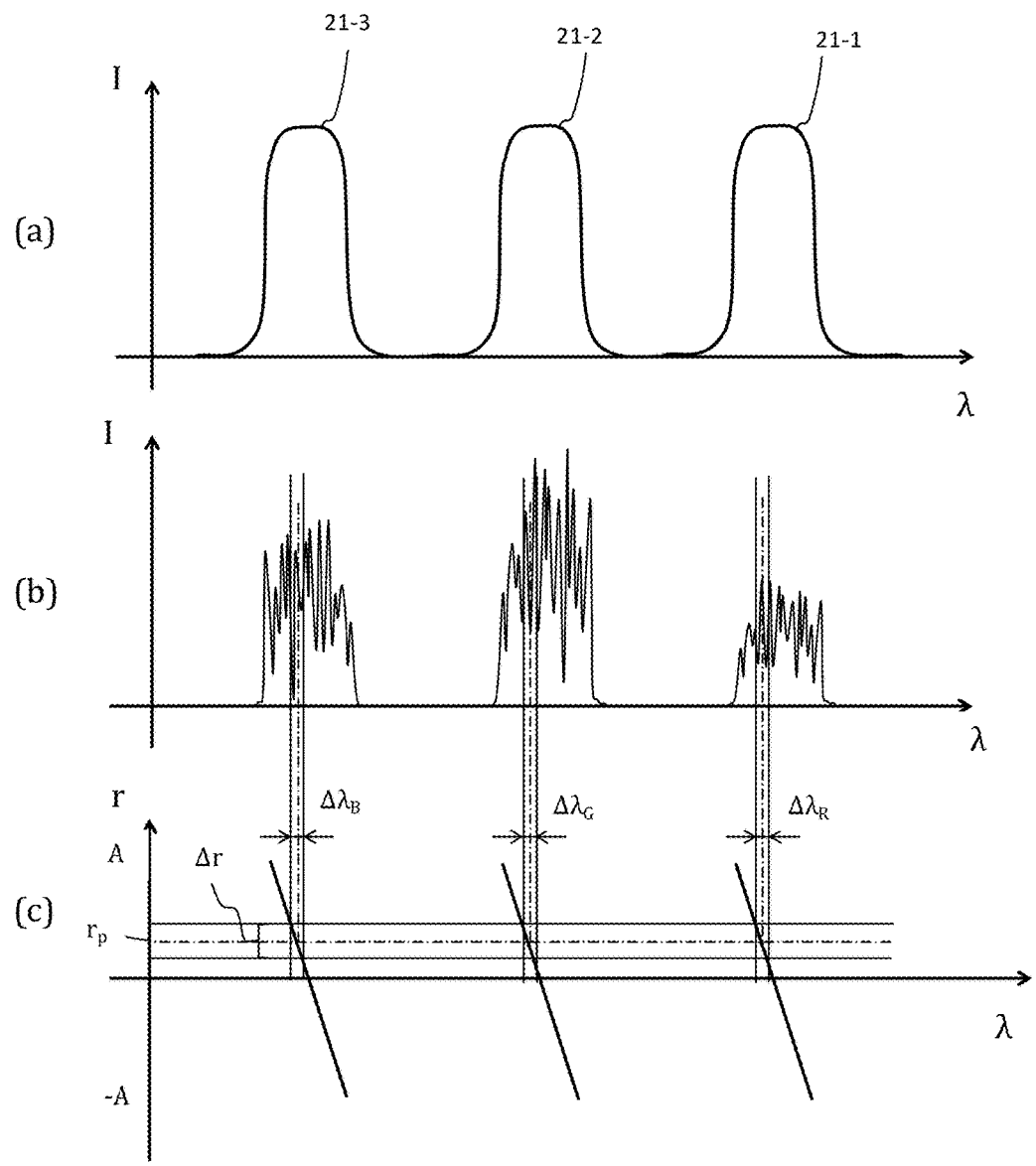
FIG. 38(a) illustrates spectral distribution of illumination light.
FIG. 38(b) illustrates spectral distribution of returning light from a subject.
FIG. 38(c) illustrates the relationship between wavelength and r.

A method of acquiring color information of the point P(r, θ) on the subject region from the relationship between the wavelength and r, using this nature, will be described with reference to FIGS. 38(a) through 43. FIG. 38(a) illustrates spectral distribution of illumination light, FIG. 38(b) illustrates spectral distribution of returning light from a subject (e.g., such as the subject 9), and FIG. 38(c) illustrates the relationship between wavelength and r. FIG. 38(a) illustrates in order from the short wavelength side, the spectral distribution 21-3 of the focal point spectrum 20-3, the spectral distribution 21-2 of the focal point spectrum 20-2, and the spectral distribution 21-1 of the focal point spectrum 20-1. These returning lights from the illuminated subject (e.g., such as the subject 9) have the distributions illustrated in FIG. 38(b) where the spectral reflectance of each wavelength region, R, G, and B, of the subject (e.g., such as the subject 9), has been reflected therein.

At point P(r, θ), there is a finite size of the illumination light. A small bandwidth of light (Δλ) can be reflected, and the returning light is detected. Because of the finite width of A λ, there can be a small spectroscopic distribution of the returning light which is detected as described herein. In some embodiments the spectroscopic distribution data from point P(r, θ), can be used in the recovery of a color image to improve color imaging. In non-color modes, one particular position is assumed to receive one specific wavelength. As the area of that position is increased, the spectrometer distribution from that finite position also increases. While this lowers resolution, assigning Δ pixels (e.g., 3 pixels) to be one "finite point" on the sample allows for a small but measurable spectroscopic distribution of reflectance within that position.

Figure 39:
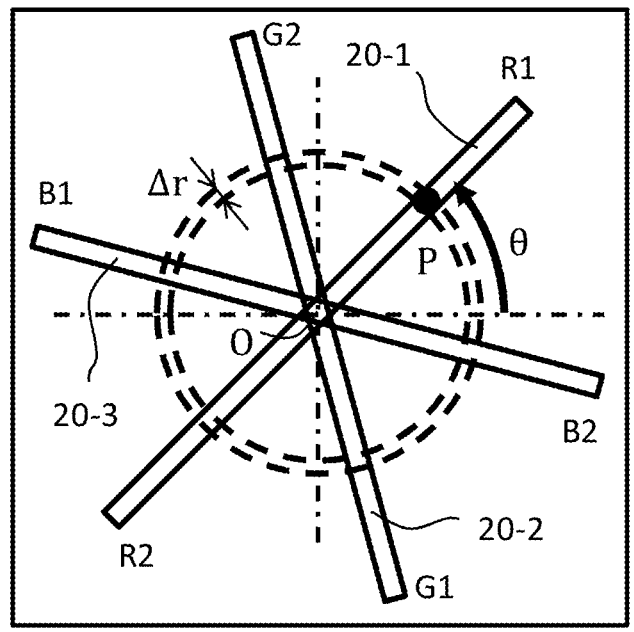
FIG. 39 illustrates a state in which focal point spectrum 20-1 is illuminating point P.

As illustrated in FIG. 32, when the probe optical system rotates in the counter-clockwise direction by angle δ until where the relationship of δ=0 is precisely true, the point P($r_p$, θ) is illuminated by the focal point spectrum 20-1. This is illustrated in FIG. 39. Note that the spectral distribution of the focal point spectrum 20-1 is denoted by 21-1 in FIG. 38(a), with the wavelength λ of the light illuminating the illumination position $r_p$ in the radial direction on the focal point spectrum 20-1 being uniquely determined by the above expression (2), as described earlier. Inversely, the data processor 15 can identify the illumination position $r_p$ from the wavelength λ.

Figure 40:
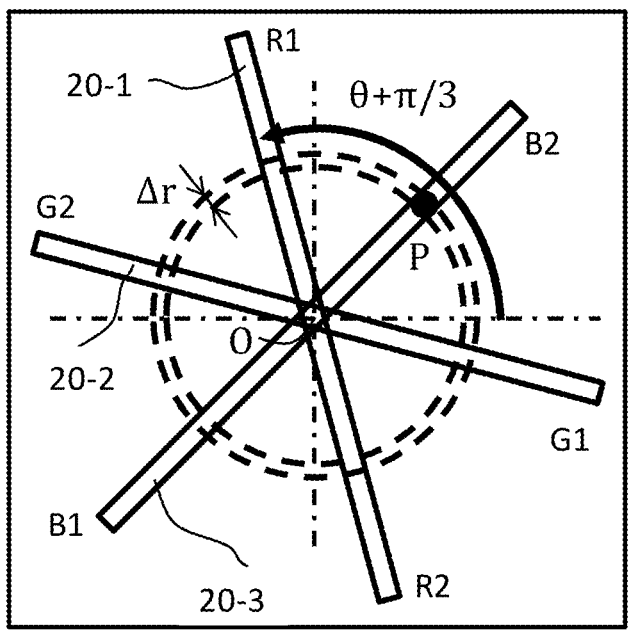
FIG. 40 illustrates a state in which focal point spectrum 20-3 is illuminating point P.

In the same way, when the probe optical system rotates in the counter-clockwise direction by angle δ+π/3, the point P($r_p$, θ) is illuminated by the focal point spectrum 20-3, as illustrated in FIG. 40. Note that the spectral distribution of the focal point spectrum 20-3 is denoted by 21-3 in FIG. 38(a), with the wavelength λ of the light illuminating the illumination position r in the radial direction on the focal point spectrum 20-3 being uniquely determined.

Figure 41:
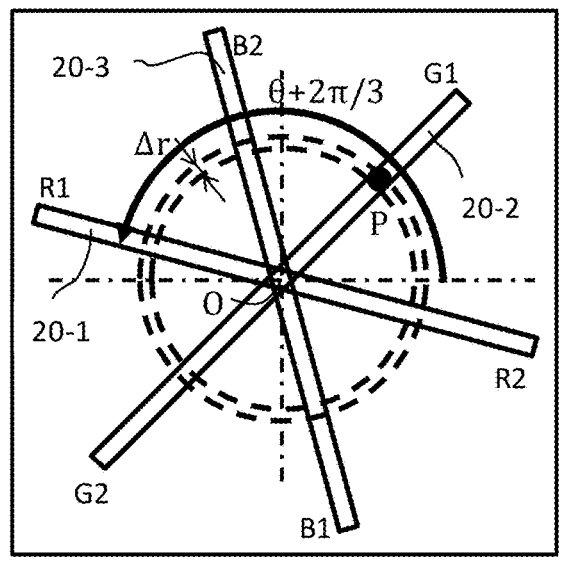
FIG. 41 illustrates a state in which focal point spectrum 20-2 is illuminating point P.
Figure 42:
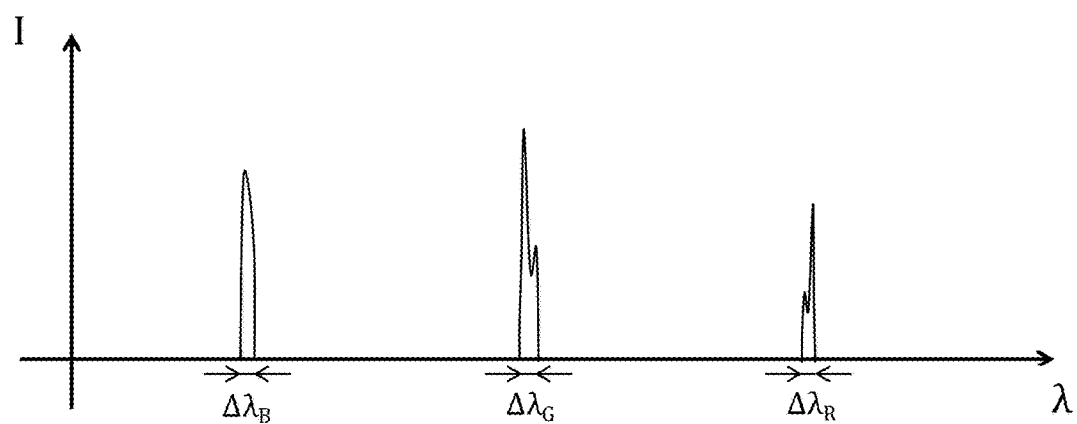
FIG. 42 illustrates spectral distribution at point P.

Further, when the probe optical system rotates in the counter-clockwise direction by angle δ+2π/3, the point P($r_p$, θ) is illuminated by the focal point spectrum 20-2, as illustrated in FIG. 41. Note that the spectral distribution of the focal point spectrum 20-2 is denoted by 21-2 in FIG. 38(a), with the wavelength λ of the light illuminating the illumination position $r_p$-s in the radial direction on the focal point spectrum 20-2 being uniquely determined, as described above. In the same way, when the probe optical system further rotates in the counter-clockwise direction by angles (δ+π), (δ+4π/3), and (δ+5π/3), the returning lights of the wavelengths corresponding to the position of point P($r_p$, θ) are acquired from the focal point spectrums 20-1, 20-3, and 20-2. The spectral distribution of the subject at point P($r_p$, θ), acquired while the probe optical system makes one rotation in this way, is as illustrated in FIG. 42.

Figure 43:
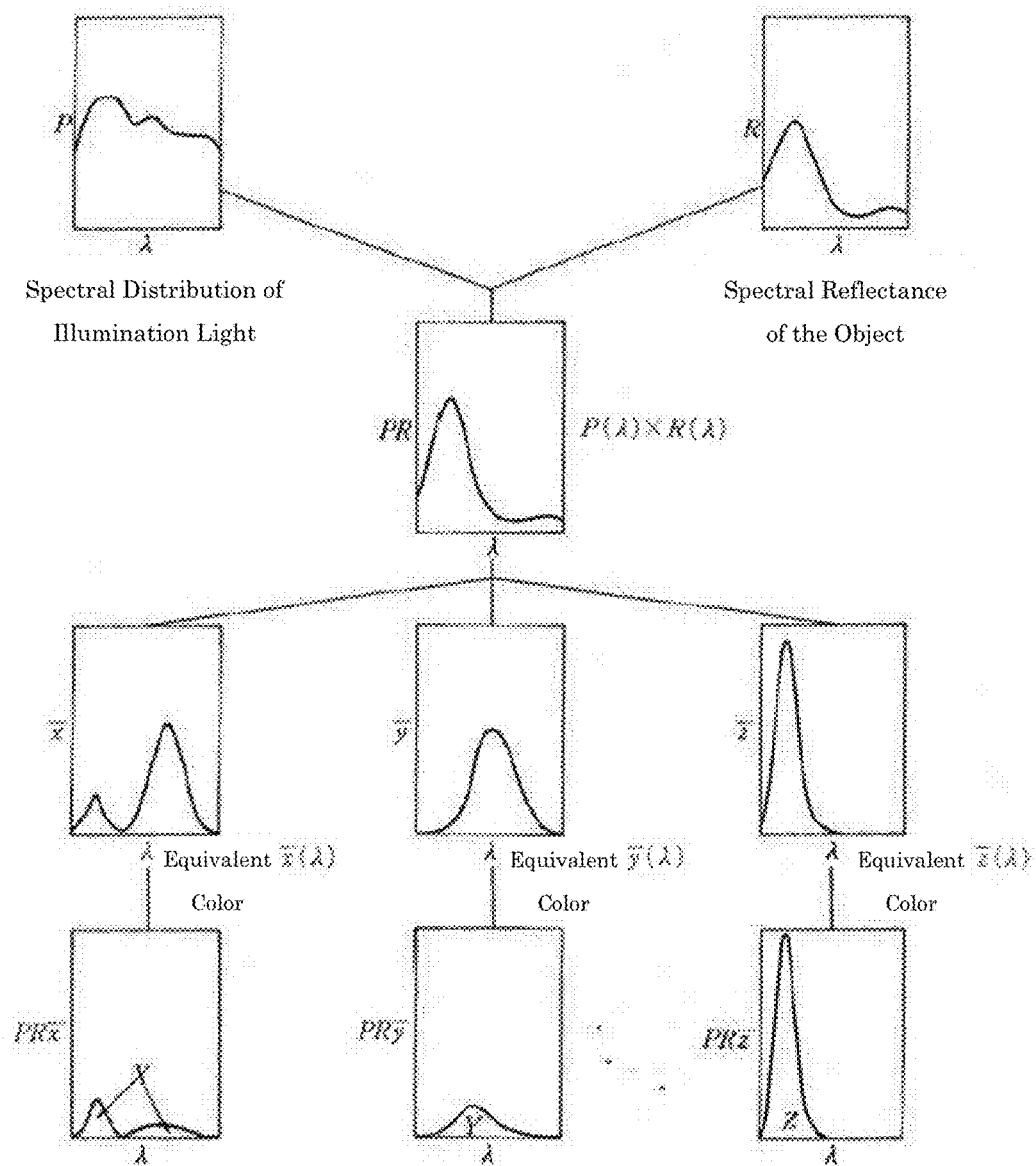
FIG. 43 illustrates calculation procedures for tristimulus values X, Y, and Z, described in Noboru Ohta, "Color Engineering (Second Publication)", published by Tokyo Denki University Press.

Next, a method for performing colorimetry of the point P from a spectral distribution of the point P acquired in this way will be described. FIG. 43 illustrates calculation procedures for tristimulus values X, Y, and Z of color, described in Noboru Ohta, "Color Engineering (Second Publication)", published by Tokyo Denki University Press. X, Y, and Z here are the parameters of the XYZ color coordinate system stipulated by the International Commission on Illumination (CIE), the widely used xy chromaticity diagram being color represented by proportion of the tristimulus values X, Y, and Z. The spectral data denoted by P(λ)×R(λ) in FIG. 43 is the spectral distribution of returning light from an object, and the distributions illustrated in FIG. 42 correspond thereto. The tristimulus values X, Y, and Z are obtained as the result of integrating regarding λ the spectral distribution with the product of functions of the three color-matching functions $\bar{x}(\lambda)$, $\bar{y}(\lambda)$, and $\bar{z}(\lambda)$, which take into consideration human luminous sensitivity. The tristimulus values X, Y, and Z are converted into x and y yielded from the expressions $$x = \frac{X}{X+Y+Z} \quad (3)$$

$$y = \frac{Y}{X+Y+Z} \quad (4)$$

and the color of the point P can be identified as one point (x,y) on the xy chromaticity diagram.

Repeatedly performing this colorimetry calculation on optional points P on the subject (such as the subject 9) regarding all combinations which r and θ can assume enables full-color information of the entire subject (such as the subject 9) to be acquired, so the subject (such as the subject 9) can be expressed in a full-color image. Note that the above-described colorimetry calculation procedures are stored in the data processor 15 beforehand and executed at high speed, so full-color images can be acquired and played as moving images, and consequently the present device embodiment can be used as a full-color endoscope.

Specifically, the CPU 1501 calculates color information by multiplying the spectral distribution acquired regarding point $P(r_p, \theta)$ (FIG. 42) by $P(\lambda) \times R(\kappa)$ of the illumination light stored in the storage/RAM 1502 beforehand. Similar computation processing is performed by the CPU 1501 on all points $P(r_p, \theta)$, to reconstruct the entire color image, which is displayed on a display via the monitor interface 1504. Alternatively, another colorimetry information calculation method is for the CPU 1501 to calculate the color mixture ratio of the RGB values from the returning light values for the six wavelengths that are acquired, and estimate the general color in a simple manner from the color mixture ratio.

According to the present embodiment, full-color imaging can be realized while retaining the greatest advantage of SEE, which is the extremely narrow diameter. Note that the above-described embodiment is only a representative example, and that various modifications and alterations may be made to the embodiment when carrying out the present disclosure.

Additional Details

In other embodiments, one color band may be optimized for viewing autofluorescence or for viewing a fluorescent dye, and the other band(s) can be optimized for viewing the tissue structure. In yet other embodiments, the color bands and/or the colors as displayed can be optimized to increase contrast between tumor, blood, or other structure of interest and the background tissue structure. For example, the background and structure of interest can be displayed as complementary colors on a color wheel.

Thus, the present disclosure also includes systems comprising the apparatus as provided herein and a device for color contrast adjustment. This device may be, for example, a computer running software processes for color contrast adjustment.

Some embodiments also include actuation. The actuation unit, or the means for actuating, may include, for example, a short-stroke electromagnetic actuator and/or a long-stroke electromagnetic actuator that moves the apparatus to a predetermined position. The actuation unit may include multiple actuators, such as Lorentz force actuators.

The probe may also comprise a rotational element that provides either continuous rotation or partial rotation. In some embodiments, the rotational element comprises a rotary junction, a galvo motor, and/or other means for rotating the illumination part. Thus, the probe may be continually rotated or, in some exemplary embodiments, it is possible that the probe can be rotated, e.g., +/−approximately 360 degrees back and forth. In other exemplary embodiments, the exemplary probe can be rotated +/−approximately 180 degrees back and forth. In further exemplary embodiments, other degrees of rotation can be used, such as, e.g., 90° degrees or 270 degrees.

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., a central processing unit (CPU), a micro processing unit (MPU), etc.) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), a Blu-ray Disc (BD)™, etc.), a flash memory device, a memory card, and the like. An I/O interface can be used to provide communication interfaces to input and output devices, which may include a keyboard, a display, a mouse, a touch screen, a touchless interface (e.g., a gesture recognition device), a printing device, a light pen, an optical storage device, a scanner, a microphone, a camera, a drive, a communication cable and a network (either wired or wireless).

The detector interface also provides communication interfaces to input and output devices. The detector may include, for example a photomultiplier tube (PMT), a photodiode, an avalanche photodiode detector (APD), a charge-coupled device (CCD), multi-pixel photon counters (MPPC), or other suitable detector device. Also, the function of the detector may be realized by computer executable instructions (e.g., one or more programs) recorded on a Storage/RAM.

In referring to the description, specific details are set forth in order to provide a thorough understanding of the examples disclosed. In other instances, well-known methods, procedures, components and circuits have not been described in detail as not to unnecessarily lengthen the present disclosure.

Exemplary embodiments have been described above with reference to the several drawings, wherein like reference numerals designate identical or corresponding parts throughout the several views and embodiments. Accordingly, descriptions of such parts with like reference numerals have not been repeated with respect to multiple figures.

It should be understood that if an element or part is referred to herein as being "on", "against", "connected to", or "coupled to" another element or part, then it can be directly on, against, connected or coupled to the other element or part, or intervening elements or parts may be present (e.g., the element or part may be indirectly on, against, connected or coupled to the other element or part). In contrast, if an element is referred to as being "directly on", "directly connected to", or "directly coupled to" another element or part, then there are no intervening elements or parts present. When used, "and/or" language includes any and all combinations of one or more of the associated listed items, if so provided.

Spatially relative terms, such as "under", "beneath", "below", "lower", "above", "upper", "proximal", "distal", and the like, may be used herein for ease of description to describe one element's or feature's relationship to another element(s) or feature(s) as illustrated in the various figures.

It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

As used herein, the terms "about" or "approximately" mean within an acceptable range for the particular parameter specified as determined by one of ordinary skill in the art, which will depend in part on how the value is measured or determined, e.g., the limitations of the sample preparation and measurement system. For example (and while not limited to the subject example(s)), "about" can mean a range of up to 20% of a given value, and more preferably means a range of up to 10%.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed herein could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected, and it is to be understood that each specific element includes all technical equivalents that operate in a similar manner. It is apparent that variations and modifications of the disclosure can be made without departing from the spirit or scope of the disclosure. Upon further study of the specification, further aspects, objects and advantages of this disclosure will become apparent to those skilled in the art.

While the above description provides examples and specific details of various embodiments, it will be appreciated that some features and/or functions of the described embodiments admit to modification without departing from the scope of the described embodiments. The above description is intended to be illustrative of one or more embodiments of the invention(s), the scope of which is limited only by the language of the claims appended hereto.

The section headings used herein are for organizational purposes only and are not to be construed as limiting the subject matter described in any way.

While the applicant's teachings are described in conjunction with various embodiments, it is not intended that the applicant's teachings be limited to such embodiments. On the contrary, the applicant's teachings encompass various alternatives, modifications, and equivalents, as will be appreciated by those of skill in the art.

The invention claimed is:

1. An apparatus comprising:
    an illumination unit having at least a first spectrally dispersive grating that is a first facet of a pyramid and a second spectrally dispersive grating that is a second facet of the pyramid structured and positioned such that a first band of spectrally dispersed light propagating from the first spectrally dispersive grating propagates on a different plane than a second band of spectrally dispersed light propagating from the second spectrally dispersive grating,
    one or more detection waveguides configured to receive a first reflected light and a second reflected light reflected by a sample; and
    one or more detection units configured to:
        detect and correlate the first and second reflected lights and form one or more images with information of at least two colors of light,
        detect and connect a field of view of light and form one or more images with the connected field of view, or
        detect and correlate the first and second reflected lights and form one or more images with information obtained by the one or more detection units at different times,
    wherein the apparatus is configured such that the first and second bands of spectrally dispersed light are spatially separated when incident on the sample.

2. The apparatus of claim 1, wherein the first and second bands of spectrally dispersed light:
    illuminate a same position on the sample at different times when the at least the first and the second spectrally dispersive gratings are rotated,
    cover different diffraction angles, or
    illuminate a same azimuthal angle at different times when the at least the first and the second spectrally dispersive gratings are rotated.

3. The apparatus of claim 2, further comprising a rotational element.

4. The apparatus of claim 1, further comprising a broadband light source and one or more light guiding components configured and positioned to direct light into the at least the first and the second spectrally dispersive gratings.

5. The apparatus of claim 1, wherein one or more of the following:
    (i) at least the first spectrally dispersive grating of the pyramid and the second spectrally dispersive grating of the pyramid are on different planes or are on planes that are not parallel to each other;
    (ii) at least the first spectrally dispersive grating of the pyramid and the second spectrally dispersive grating of the pyramid have different groove densities;
    (iii) the groove densities of the first and second spectrally dispersive gratings differ from one another by at least 200 lines/mm;
    (iv) the pyramid does not have a vertex at a center thereof; and
    (v) the pyramid has its vertex at one point on a circumference of an outer circle or on an edge of the illumination unit or of the gratings.

6. The apparatus of claim 1, wherein one or more of the following:
   (i) the first and second gratings have patterns that are repeated at least two times each on the grating configuration;
   (ii) the second spectrally dispersive grating has a grating vector at an angle of between 5 degrees and 20 degrees from the grating vector of the first spectrally dispersive grating; and
   (iii) the at least the first and second spectrally dispersive gratings have a different pitch.

7. The apparatus of claim 1, further comprising:
   a third spectrally dispersive grating that is a third facet of the pyramid, wherein a third band of light propagating from the third spectrally dispersive grating propagates on a different plane than either the first or second bands of light,
   wherein the one or more detection waveguides are further configured to receive a third reflected light reflected by the sample, and
   wherein the one or more detection units are configured to detect and correlate the first, second, and third reflected lights and form one or more images with information of at least three colors of light.

8. The apparatus of claim 7, wherein one or more of the following:
   (i) at least the first spectrally dispersive grating of the pyramid, the second spectrally dispersive grating of the pyramid and the third spectrally dispersive grating of the pyramid are on different planes or are on planes that are not parallel to each other;
   (ii) at least the first, second, and third spectrally dispersive gratings have the same angle with respect to an axis of rotation; and
   (iii) at least the first, second, and third spectrally dispersive gratings have three different facet angles so lights incident on the spectrally dispersive gratings have different diffraction angles.

9. The apparatus of claim 1, further comprising one or more of the following:
   (i) an actuation unit;
   (ii) a single detection fiber or three or more detection fibers;
   (iii) one or more switches that alternate illumination from the first and second spectrally dispersive gratings; and
   (iv) an optical element positioned such that a light reflected by a tissue or the sample reflects off of or is angled by the optical element before it is incident on the one or more detection waveguides.

10. The apparatus of claim 1, wherein one or more of the following:
    (i) the one or more detection units are configured to detect and correlate the first and second reflected lights and form one or more images based on the first and second reflected lights collected from the same spatial location on the sample at different times;
    (ii) the one or more detection waveguides include an optical fiber positioned such that a reflected light reflected by the sample of the first and second reflected lights travels through at least one spectrally dispersive grating of the at least the first and second spectrally dispersive gratings before the light reflected by the sample is incident on the detection optical fiber, or the one or more detection waveguides include an optical fiber positioned such that a reflected light reflected by the sample of the first and second reflected lights is incident on the optical fiber without previously traveling through a spectrally dispersive grating;
    (iii) the apparatus is configured and structured such that a field angle of a light entering the one or more detection waveguides is smaller than a field angle of the diffracted light having the first wavelength and the diffracted light having the second wavelength;
    (iv) the one or more detection waveguides comprise an angle-polished optical fiber configured such that the detection field of the detection optical fiber substantially overlaps the illumination field of the apparatus; and
    (v) respective or relative areas of the first and second spectrally dispersive gratings are sized to compensate for a spectral intensity distribution of a light source.

11. The apparatus of claim 1, wherein the sample is an in vivo tissue sample.

12. A probe comprising:
    a light guiding component,
    a light focusing component,
    a rotational element, and
    a grating configuration that comprises at least three spectrally dispersive grating patterns located on at least three facets of a pyramid, wherein bands of spectrally dispersed light propagating from the at last three spectrally dispersive grating patterns propagate on different planes and are incident on a sample at different spatial positions,
    wherein the light guiding component and the light focusing component operate to deliver light to the granting configuration for the bands of spectrally dispersed light, and the rotational element operates to rotate one or more of: the grating configuration, the light focusing component, or the light guiding component.

13. The probe of claim 12, wherein one or more of the following:
    (i) the at least three spectrally dispersive grating patterns are on different planes or are on planes that are not parallel to each other;
    (ii) the at least three spectrally dispersive grating patterns have the same angle with respect to an axis of rotation; and
    (iii) the at least three spectrally dispersive grating patterns have three different facet angles so lights incident on the spectrally dispersive gratings have different diffraction angles.

14. The probe of claim 12, wherein the bands of spectrally dispersed light propagating from the at least three spectrally dispersive grating patterns:
    illuminate a same position on the sample at different times when the at least three spectrally dispersive grating patterns are rotated,
    cover different diffraction angles, or
    illuminate a same azimuthal angle at different times when the at least three spectrally dispersive grating patterns are rotated.

15. The probe of claim 12, wherein the sample is an in vivo tissue sample.

* * * * *